US009038629B2

(12) United States Patent
Smith et al.

(10) Patent No.: US 9,038,629 B2
(45) Date of Patent: *May 26, 2015

(54) HUMIDIFIER AND/OR FLOW GENERATOR FOR CPAP DEVICE

(75) Inventors: Ian Malcolm Smith, Westleigh (AU); John Michael Snow, Cremorne (AU); Perry David Lithgow, Glenwood (AU); Dan Kao, Chatswood (AU)

(73) Assignee: ResMed Limited, Bella Vista (AU)

( * ) Notice: Subject to any disclaimer, the term of this patent is extended or adjusted under 35 U.S.C. 154(b) by 2089 days.

This patent is subject to a terminal disclaimer.

(21) Appl. No.: 11/988,870

(22) PCT Filed: Aug. 15, 2006

(86) PCT No.: PCT/AU2006/001170
§ 371 (c)(1),
(2), (4) Date: Feb. 27, 2009

(87) PCT Pub. No.: WO2007/019625
PCT Pub. Date: Feb. 22, 2007

(65) Prior Publication Data
US 2009/0194106 A1 Aug. 6, 2009
US 2011/0283999 A2 Nov. 24, 2011

Related U.S. Application Data

(60) Provisional application No. 60/707,948, filed on Aug. 15, 2005.

(51) Int. Cl.
*A61M 16/10* (2006.01)
*A61M 16/08* (2006.01)
(Continued)

(52) U.S. Cl.
CPC ............ *A61M 16/0816* (2013.01); *B01D 47/02* (2013.01); *A61M 16/10* (2013.01);
(Continued)

(58) Field of Classification Search
CPC .................. A61M 16/0075; A61M 16/0816; A61M 16/10; A61M 16/1075; A61M 16/109; A61M 16/16; A61M 2205/42; B01D 47/02

USPC ............ 128/200.24, 203.12, 203.16, 203.17, 128/203.26, 203.27, 204.14, 204.17, 128/204.18, 204.21; 604/257, 291; 219/429–433, 436, 465.1; 392/394, 392/403, 444; 261/119.1, 142
See application file for complete search history.

(56) References Cited

U.S. PATENT DOCUMENTS 1,475,289 A    11/1923   Diescher
2,500,404 A    3/1950    Donnelly
(Continued)

FOREIGN PATENT DOCUMENTS

EP    0 339 234 A1    11/1989
EP    1 138 341       10/2001
(Continued)

OTHER PUBLICATIONS

"Lid". Collins English Dictionary. 2000. http://www.credoreference.com/entry/hcengdict/either (Feb. 24, 2014).*
(Continued)

*Primary Examiner* — Tan-Uyen (Jackie) T Ho
*Assistant Examiner* — Mark K Han
(74) *Attorney, Agent, or Firm* — Nixon & Vanderhye P.C.

(57) ABSTRACT

A CPAP device includes a humidifier including humidifier tub having a heat conducting base plate; and a cradle to support the humidifier tub in an operative position. The cradle may also support a flow generator in operative relation to the humidifier tub. The cradle includes a heater plate in communication with the heat conducting base plate of the humidifier tub in use. The cradle further includes a retaining mechanism to retain the humidifier tub in the cradle, the retaining mechanism being structured to force the base plate into engagement with the heater plate. The humidifier and/or flow generator may include various features to manage inadvertent backspill of water from the humidifier to the flow generator.

82 Claims, 20 Drawing Sheets

(51) Int. Cl.
*A61M 16/16* (2006.01)
*A61M 16/00* (2006.01)
*B01D 47/02* (2006.01)

(52) U.S. Cl.
CPC ............ *A61M16/1075* (2013.01); *A61M 16/16* (2013.01); *A61M 2205/42* (2013.01); *A61M 16/0075* (2013.01); *A61M 16/109* (2014.02)

(56) References Cited

U.S. PATENT DOCUMENTS

| | | | |
|---|---|---|---|
| 2,872,560 A * | 2/1959 | Bowles | 219/433 |
| 2,998,198 A | 8/1961 | Young | |
| 3,090,380 A | 5/1963 | Dold | |
| 3,275,344 A | 9/1966 | Kendt | |
| 3,388,705 A * | 6/1968 | Grosshandler | 128/207.14 |
| 4,000,341 A | 12/1976 | Matson | |
| 4,028,444 A * | 6/1977 | Brown et al. | 261/122.1 |
| 4,049,233 A | 9/1977 | Brandin | |
| 4,124,046 A | 11/1978 | Lundberg | |
| 4,164,645 A * | 8/1979 | Dogliotti | 219/447.1 |
| 4,165,456 A * | 8/1979 | Dogliotti | 219/447.1 |
| 4,201,737 A | 5/1980 | Carden | |
| 4,203,027 A * | 5/1980 | O'Hare et al. | 392/390 |
| 4,286,815 A | 9/1981 | Clark | |
| 4,496,132 A | 1/1985 | Winegarten | |
| 4,557,261 A | 12/1985 | Rügheimer | |
| 4,575,128 A | 3/1986 | Sundquist | |
| 4,921,642 A | 5/1990 | LaTorraca | |
| 4,953,897 A * | 9/1990 | Klober | 285/226 |
| 5,329,939 A | 7/1994 | Howe | |
| 5,349,946 A | 9/1994 | McComb | |
| 5,564,415 A | 10/1996 | Dobson et al. | |
| 5,673,687 A | 10/1997 | Dobson et al. | |
| 5,943,473 A * | 8/1999 | Levine | 392/401 |
| 6,024,694 A * | 2/2000 | Goldberg et al. | 600/22 |
| 6,438,180 B1 | 8/2002 | Kavcic et al. | |
| 6,554,260 B1 | 4/2003 | Lipscombe et al. | |
| 6,648,664 B1 | 11/2003 | McHugh et al. | |
| 6,718,974 B1 * | 4/2004 | Moberg | 128/204.14 |
| 6,811,546 B1 | 11/2004 | Callas et al. | |
| 6,843,207 B2 * | 1/2005 | Kanzaki et al. | 122/31.1 |
| 6,935,337 B2 | 8/2005 | Virr et al. | |
| 6,988,497 B2 * | 1/2006 | Levine | 128/203.27 |
| 7,137,388 B2 * | 11/2006 | Virr et al. | 128/203.17 |
| D542,900 S * | 5/2007 | Snow et al. | D23/356 |
| 7,327,949 B1 * | 2/2008 | Cheng et al. | 392/444 |
| 7,413,173 B2 * | 8/2008 | DiMatteo et al. | 261/142 |
| 7,614,398 B2 | 11/2009 | Virr et al. | |
| 8,006,691 B2 * | 8/2011 | Kenyon et al. | 128/200.24 |
| 8,049,143 B2 * | 11/2011 | Andel et al. | 219/443.1 |
| 8,240,306 B2 * | 8/2012 | Cortez et al. | 128/203.27 |
| RE44,453 E | 8/2013 | Virr et al. | |
| 8,544,465 B2 * | 10/2013 | Smith et al. | 128/202.27 |
| 2002/0195110 A1 | 12/2002 | Watton | |
| 2003/0066526 A1 * | 4/2003 | Thudor et al. | 128/203.26 |
| 2003/0172931 A1 | 9/2003 | Kerechanin, II et al. | |
| 2004/0055597 A1 * | 3/2004 | Virr et al. | 128/203.12 |
| 2004/0065335 A1 | 4/2004 | Huber et al. | |
| 2004/0076412 A1 * | 4/2004 | Kanzaki et al. | 392/441 |
| 2004/0221843 A1 | 11/2004 | Baecke | |
| 2004/0226562 A1 | 11/2004 | Bordewick | |
| 2005/0178383 A1 * | 8/2005 | Mackie et al. | 128/203.16 |
| 2006/0130836 A1 * | 6/2006 | Wixey et al. | 128/204.22 |
| 2006/0237005 A1 | 10/2006 | Virr et al. | |
| 2008/0072900 A1 | 3/2008 | Kenyon et al. | |
| 2008/0302361 A1 * | 12/2008 | Snow et al. | 128/202.27 |
| 2009/0120434 A1 | 5/2009 | Smith et al. | |
| 2010/0154796 A1 * | 6/2010 | Smith et al. | 128/203.26 |
| 2011/0271956 A2 * | 11/2011 | Smith et al. | 128/202.13 |

FOREIGN PATENT DOCUMENTS

| | | |
|---|---|---|
| FR | 2 663 547 | 12/1991 |
| GB | 2 116 434 A | 9/1983 |
| GB | 2 173 107 | 10/1986 |
| GB | 2 173 108 | 10/1986 |
| WO | 99/22793 | 5/1999 |
| WO | WO 02/066107 A1 | 8/2002 |
| WO | WO 2004/043528 A1 | 5/2004 |
| WO | WO 2004112873 A1 * | 12/2004 |

OTHER PUBLICATIONS

Respironics, Inc., REMstar Heated Humidifier manual, 2001.*
Notice of Opposition to Grant of Patent filed on Jun. 27, 2011 against New Zealand Application No. 564886.
Examination Report mailed Dec. 14, 2011 in New Zealand Appln. No. 586325 (3 pages).
International Search Report mailed Nov. 21, 2006.
U.S. Appl. No. 60/707,949, filed Aug. 15, 2005 (p. 6 of specification).
U.S. Appl. No. 60/707,951, filed Aug. 15, 2005 (p. 6 of specification).
New Zealand Examination Report mailed Dec. 14, 2011 in New Zealand Appln. No. 597020 (3 pages).
Examiner's First Report Mailed Mar. 23, 2011 in Australian Application No. 2006281985 (2 pages).
Examination Report mailed Jun. 29, 2010 in New Zealand Appln. No. 586325 (2 pages).
Counterstatement filed Oct. 26, 2011 in New Zealand Application No. 564886 (13 pages).
Office Action issued in Chinese Application No. 20068029792.9 on Dec. 11, 2009.
Further Examination Report mailed Mar. 4, 2013 in New Zealand Application No. 597020 (2 pages).
First Examination Report mailed Mar. 8, 2013 in New Zealand Application No. 607890 (2 pages).
Chinese Office Action mailed Jun. 18, 2013 in Chinese Application No. 201110068459.1 with English Translation (9 pages).
Extended European Search Report mailed Jul. 3, 2013 in European Application No. 06774815.2 (10 pages).
Notification of the Fourth Office Action mailed Dec. 30, 2013 in Chinese Application No. 201110068459.1, with English Translation (10 pages).
Notification of the Fifth Office Action dated Jun. 10, 2014 issued in corresponding Chinese Application No. 201110068459.1 (10 pages).
First Communication mailed May 9, 2014 in European Application No. 06774815.2 (7 pages).
Further Examination Report mailed Feb. 28, 2014 in New Zealand Application No. 607890 (2 pages).
First Examination Report mailed Feb. 28, 2014 in New Zealand Application No. 621227 (2 pages).
International Search Report mailed Sep. 18, 2006 in International Application No. PCT/AU2006/001172.
Notification of the Second Office Action mailed in Chinese Application No. 201110068459.1, with English Translation.

* cited by examiner

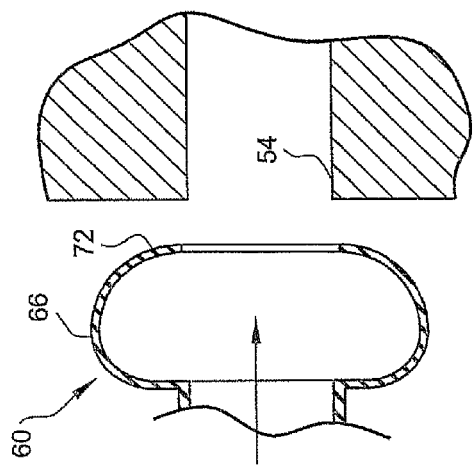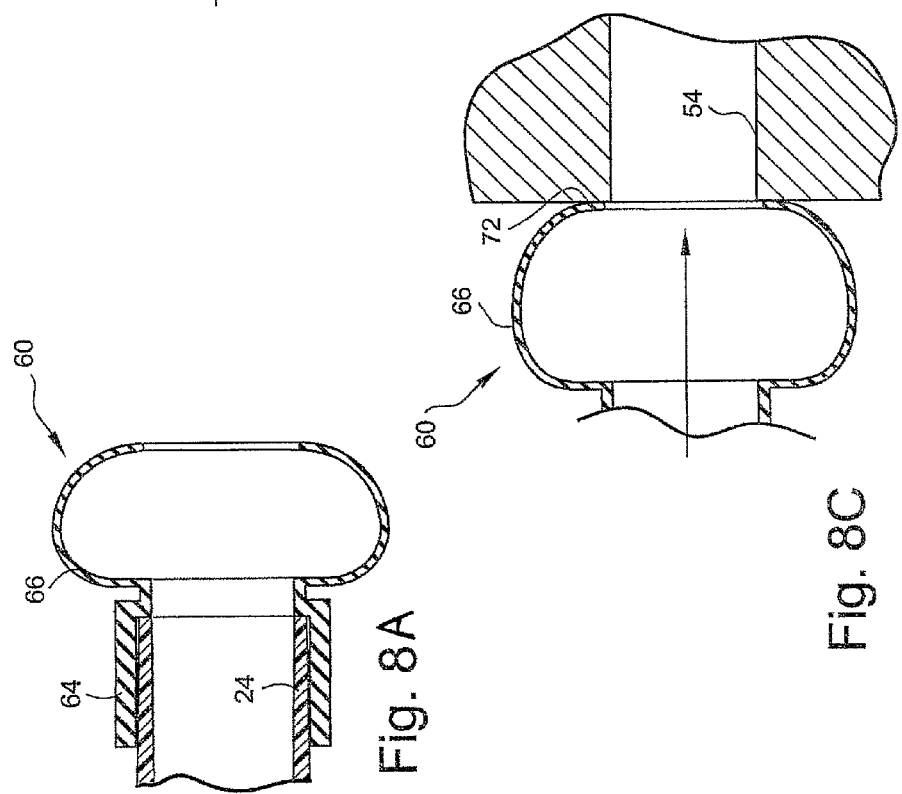

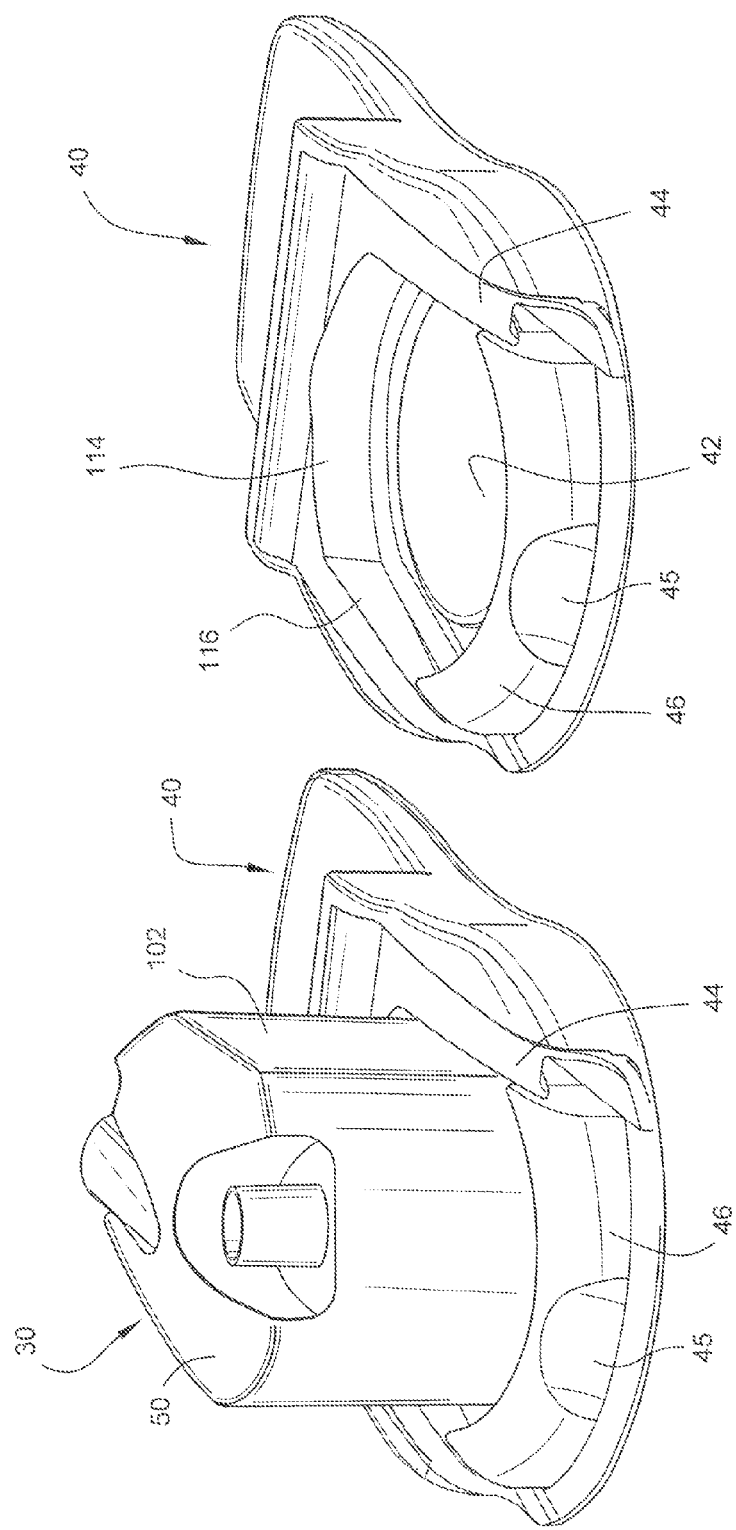

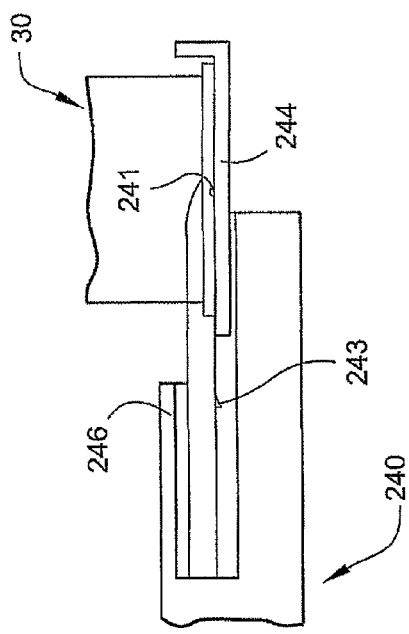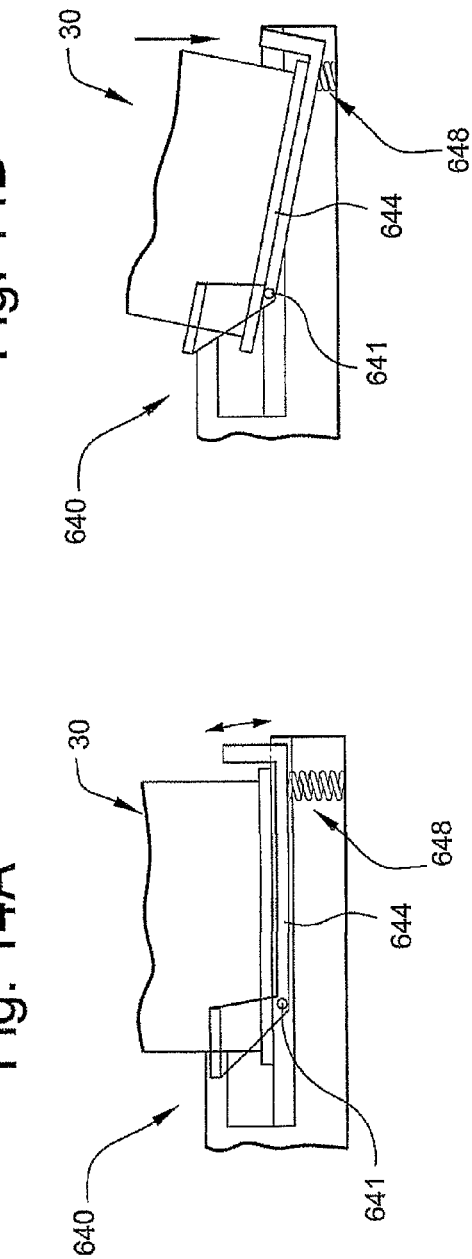

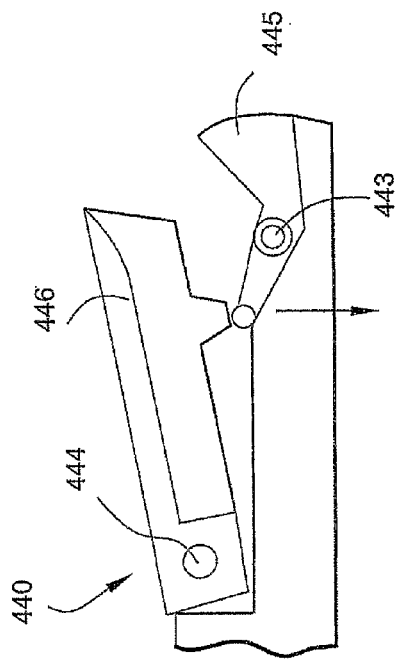
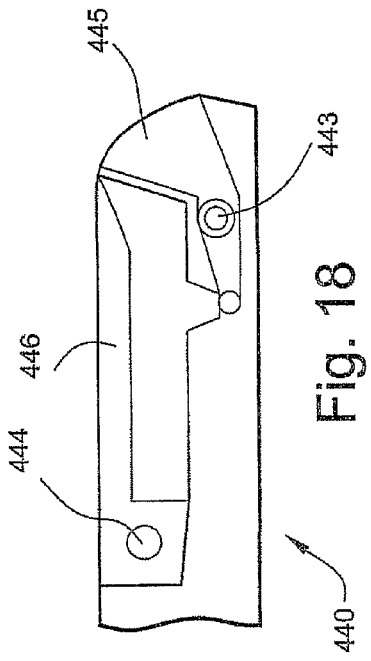
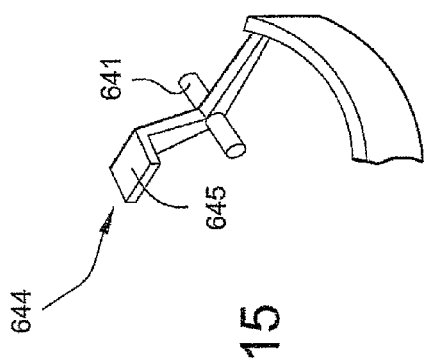
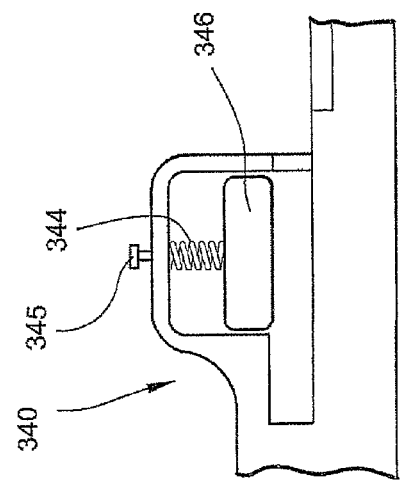

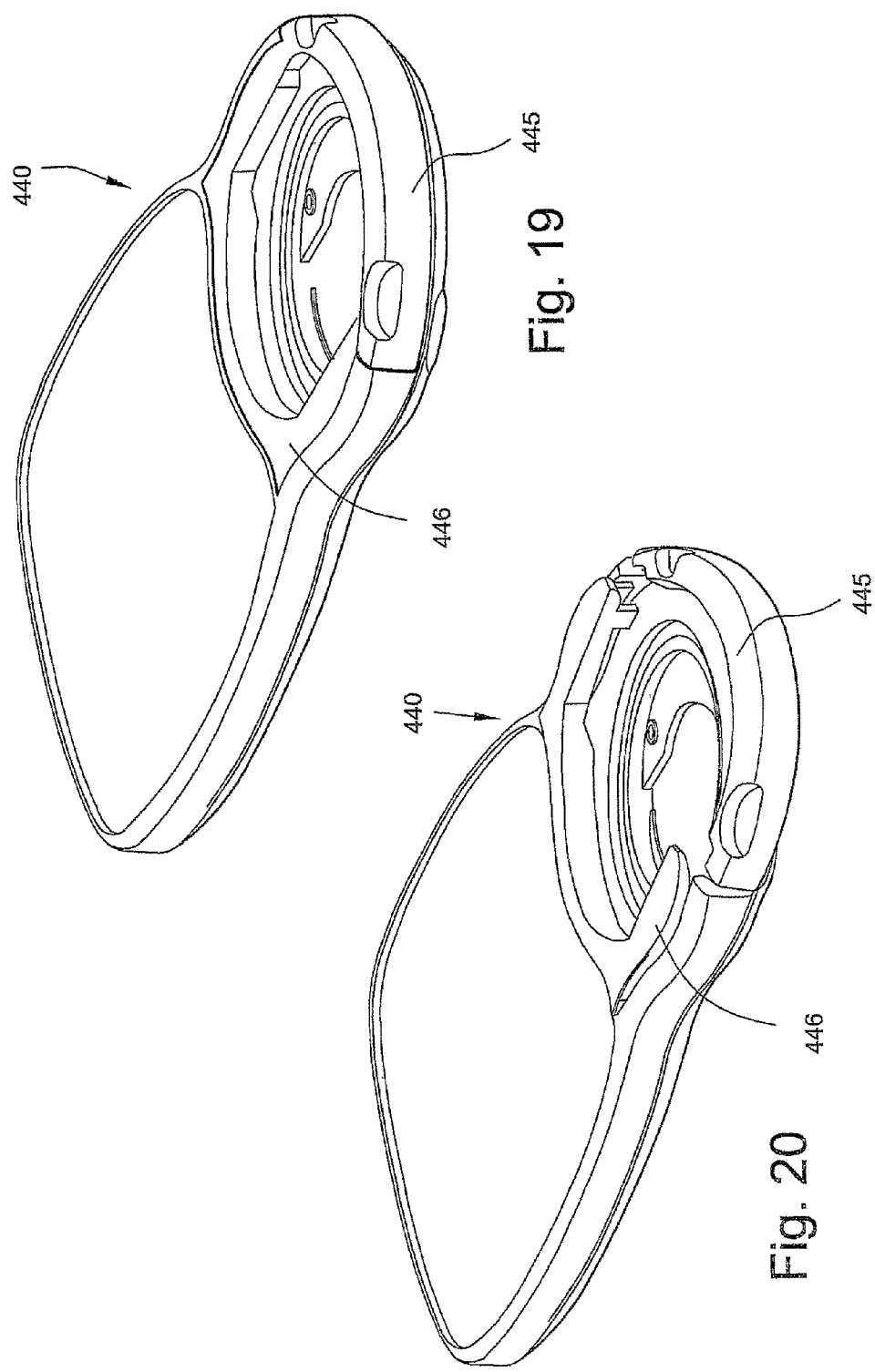

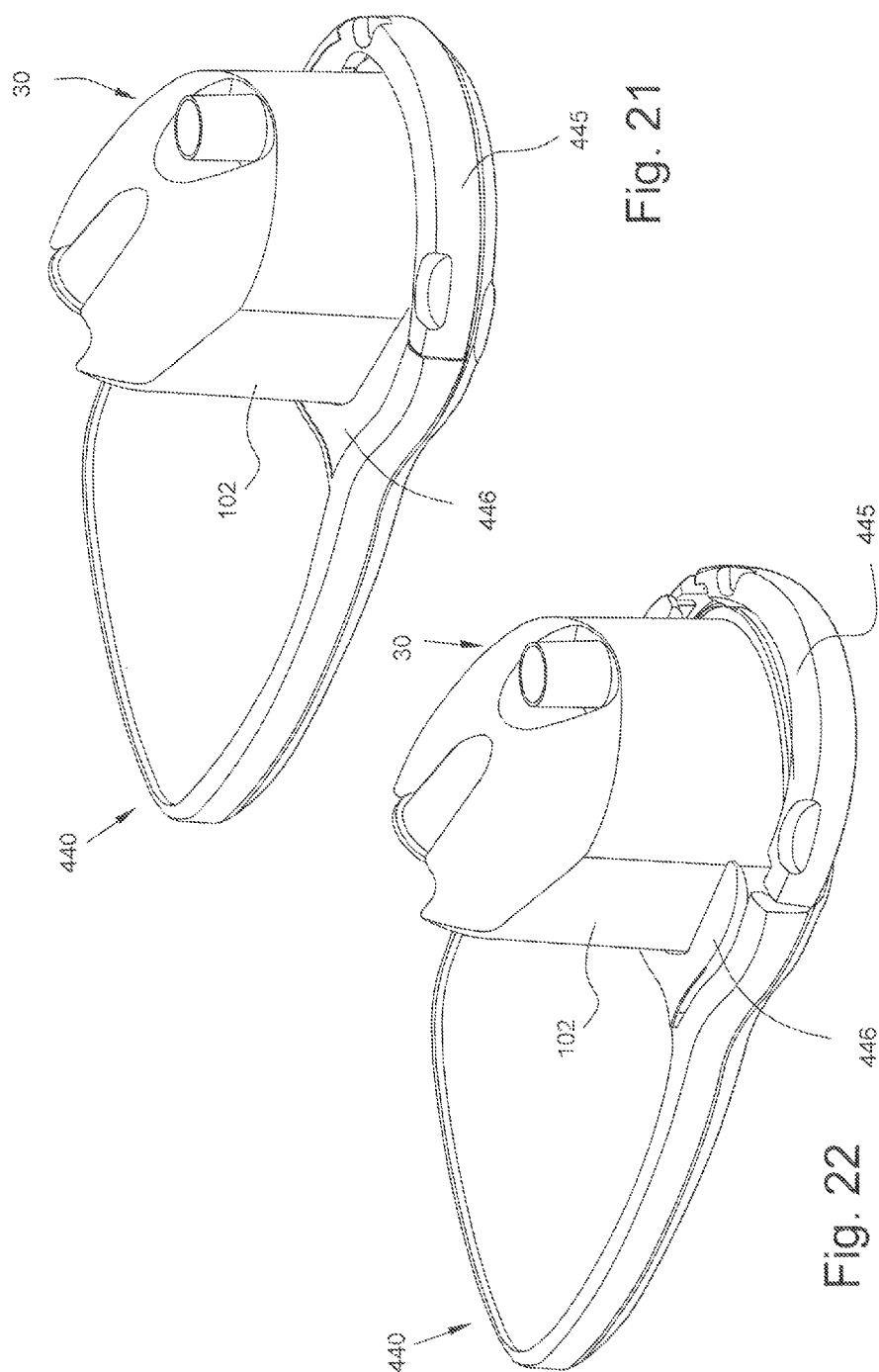

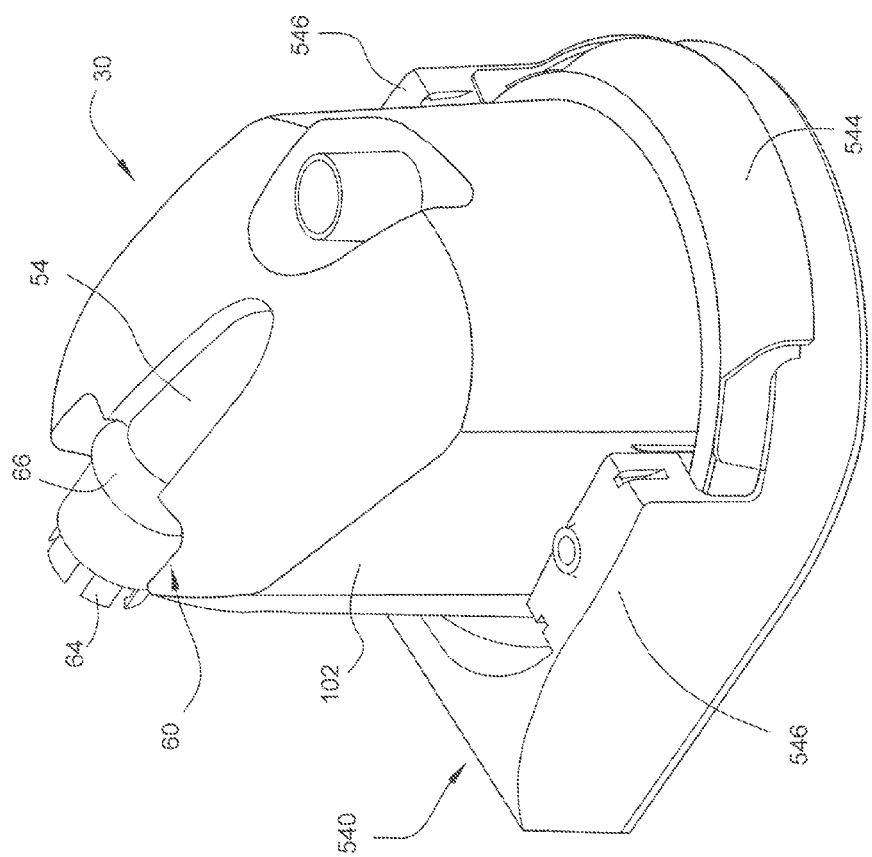

HUMIDIFIER AND/OR FLOW GENERATOR FOR CPAP DEVICE

CROSS-REFERENCE TO PRIORITY APPLICATION

This application is the U.S. national phase of International Application No. PCT/AU2006/001170, which designated the U.S. and claims the benefit to U.S. Provisional Application No. 60/707,948, filed 15 Aug. 2005, the entire contents of each of which are hereby incorporated by reference.

FIELD OF THE INVENTION

The present invention relates to a removable humidifier and/or flow generator for a Continuous Positive Airway Pressure (CPAP) device used to treat sleep disordered breathing (SDB) conditions such as Obstructive Sleep Apnea (OSA).

BACKGROUND OF THE INVENTION

Domestic treatment of OSA and other SDB is usually done using a device that provides CPAP, e.g., nasal CPAP. A common configuration of a treatment system comprises a CPAP device and a patient interface, e.g., a nasal mask. The nasal mask forms a sealing interface with the patient's nasal passages in use so that the supply of air at positive pressure from the CPAP device may be delivered to the patient's airways. In this way, while the patient is wearing a nasal mask, their mouth is uncovered.

In some situations, patients "mouth breath" during sleep. When this happens while wearing only a nasal mask, air can pass in the mask and straight out the patient's mouth. This can lead to drying of the patient's airway and patient discomfort. This patient discomfort can to some extent be alleviated by the use of a humidifier placed between the CPAP device and the patient interface.

Many humidifiers are available, although the most convenient form is one that is either integrated with or configured to be coupled to the relevant CPAP device. While passive humidifiers can provide some relief, generally a heated humidifier is required to provide sufficient moisture to the air so that patients will be comfortable. Humidifiers typically comprise a water tub having a capacity of several hundred milliliters, a heating element, a control to enable the level of humidification to be varied, an air inlet to receive air from the blower, and an air outlet adapted to be connected to an air delivery conduit so that the humidified pressurized air may be passed to the patient interface. Usually, the water tub is removable from the system so that it can be refilled when necessary.

In making a humidification tub removable, there are two problems that need to be overcome. Firstly, there is a need for an air seal between the air outlet of the flow generator and the air inlet of the humidifier tub. An air seal is important to reduce air leaks that may result in an increased pressure drop between the air pressure generated by the flow generator and the air pressure delivered to the patient at the patient interface. Secondly, for efficient humidification, there must be adequate thermal contact between the humidification tub and the heating element.

Commonly, humidifier tubs are attached either directly to a humidifier control base or to a system base or cradle that facilitates the correct assembly of the flow generator with the humidifier. Generally, the humidifier control base or the system base or cradle comprises a heating plate that contacts the base of the humidifier tub to facilitate heating of the water within the humidifier tub. Commonly, these base systems comprise a spring loaded heater plate on to which the humidifier tub is attached. The spring loaded heater plate ensures good thermal contact with the base of the humidifier tub. For example, the Fisher & Paykel HC200 system and the Respironics RemStar heated humidifier have spring loaded heater plates. However, such spring loaded heater plates can provide a friction force against insertion of the humidifier tub, which may make installation of the humidifier tub difficult for some users, especially older or frail users.

SUMMARY OF THE INVENTION

One aspect of the invention relates to a seal between the humidifier inlet and flow generator outlet.

Another aspect of the invention relates to a method and apparatus for retaining a humidifier tub for use in a CPAP device, e.g., nasal CPAP device.

Another aspect of the invention relates to a method and apparatus for providing good thermal contact between the humidifier tub and a heating element.

Another aspect of the invention relates to management of the inadvertent introduction of water into the flow generator, e.g., by tipping or overfilling the humidifier.

Yet another aspect of the invention relates to a CPAP device or humidifier including a humidifier tub including a heat conducting base plate and a cradle to support the humidifier tub in an operative position. The cradle includes a heater plate in communication with the heat conducting base plate of the humidifier tub in use. The cradle further includes a retaining mechanism to retain the humidifier tub in the cradle. The retaining mechanism is structured to force the base plate into engagement with the heater plate.

Another aspect of the present invention relates to a CPAP device including a cradle having a fixed heating plate; and a humidifier tub having a heat conducting base, the base being forcibly coupled with the fixed heating plate of the cradle upon assembly of the cradle and the humidifier tub.

Still another aspect of the invention relates to a method for retaining a humidifier tub to a cradle, comprising providing a cradle including a retaining mechanism; moving the retaining mechanism to a first position that enables insertion of the humidifier tub; providing the humidifier tub to the cradle; moving the retaining mechanism to a second position that secures the humidifier tub in an operative position; and forcing a heat conducting base plate of the humidifier tub into engagement with a heater plate of the cradle.

Another aspect of the invention relates to a CPAP device comprising a flow generator including a flow generator outlet, a motor having a motor outlet, a muffler chamber having an inlet coupled to the motor outlet and a muffler chamber outlet in communication with a flow generator outlet, wherein an axis of the motor outlet is offset from an axis of the muffler chamber outlet and/or the flow generator outlet.

Still another aspect of the invention relates to a CPAP device comprising a flow generator including a flow generator outlet, a motor having a motor outlet, a muffler chamber having an inlet coupled to the motor outlet and a muffler chamber outlet in communication with a flow generator outlet, wherein said muffler chamber includes an upper part conduit portion and a lower storage portion integrally formed with the part conduit portion.

These and other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 8A is a cross-sectional view illustrating a seal/connector according to another embodiment of the present invention;

FIGS. 8B-8C illustrate a seal/connector according to an embodiment of the present invention in use;

FIGS. 9-12 illustrate a cradle according to an embodiment of the present invention using a catch to secure the humidifier tub;

FIG. 13 illustrates a cradle according to another embodiment of the present invention using a sliding docking portion to secure the humidifier tub;

FIGS. 14A, 14B, and 15 illustrate a cradle according to another embodiment of the present invention using a pivoting docking portion to secure the humidifier tub;

FIG. 16 illustrates a cradle according to another embodiment of the present invention using a spring-biased clamping edge to secure the humidifier tub;

FIGS. 17-22 illustrate a cradle according to another embodiment of the present invention using a pivotable front guard and a pivotable humidifier retaining portion;

FIG. 26 illustrates a humidifier tub secured to the cradle shown in FIGS. 23-25, the humidifier tub engaged with the seal/connector shown in FIGS. 5-7;

DETAILED DESCRIPTION OF ILLUSTRATED EMBODIMENTS

1. CPAP Device

FIGS. 1-4 illustrate a CPAP device 10 according to an embodiment of the present invention. As illustrated, the CPAP device 10 includes a flow generator 20 and a humidifier 30 adapted to be coupled to the flow generator 20.

The humidifier may be connected to the flow generator using loop-back power and communication cables between the humidifier and the flow generator. In an alternative, the humidifier and the flow generator may communicate using a fiber optic or infrared communication system between the flow generator and the humidifier. This system may detect the presence of the humidifier tub and provide communication and power between the devices via transmitters and receivers.

2. Humidifier

Figure 9:
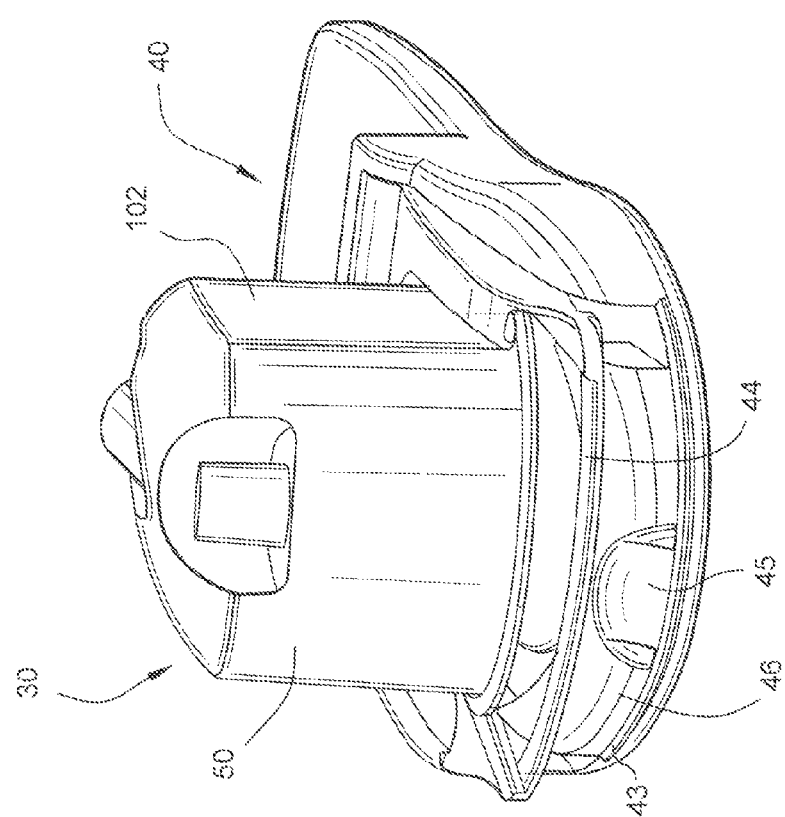

The humidifier 30 includes a humidifier tub 50 having a base plate 52 sealed to the bottom of the tub 50 and a heater element that may be formed as part of a cradle unit 40 (see FIG. 9). The heater element may also be formed as an integral part of the base plate or otherwise separate from the cradle. The tub 50 includes an inlet 54 adapted to be in fluid communication with (i.e. not necessarily directly) the outlet 24 of the flow generator 20, and an outlet 56 adapted to be connected to an air delivery conduit. The air delivery conduit includes one end coupled to the outlet 56 of the tub 50 and an opposite end coupled to a patient interface. The patient interface comfortably engages the patient's face and provides a seal. The patient interface may have any suitable configuration as is known in the art, e.g., full-face mask, nasal mask, oro-nasal mask, mouth mask, nasal prongs, etc.

The tub 50 and base plate 52 define a chamber that is adapted to receive a volume of water, e.g., several hundred milliliters. The inlet 54 and the outlet 56 are both in communication with the chamber. In use, a supply of pressurized air from the flow generator 20 enters the inlet 54 of the tub 50 and collects moisture through contact with the water within the tub 50 before continuing on to the outlet 56 and to the patient via the air delivery conduit.

Figure 1:
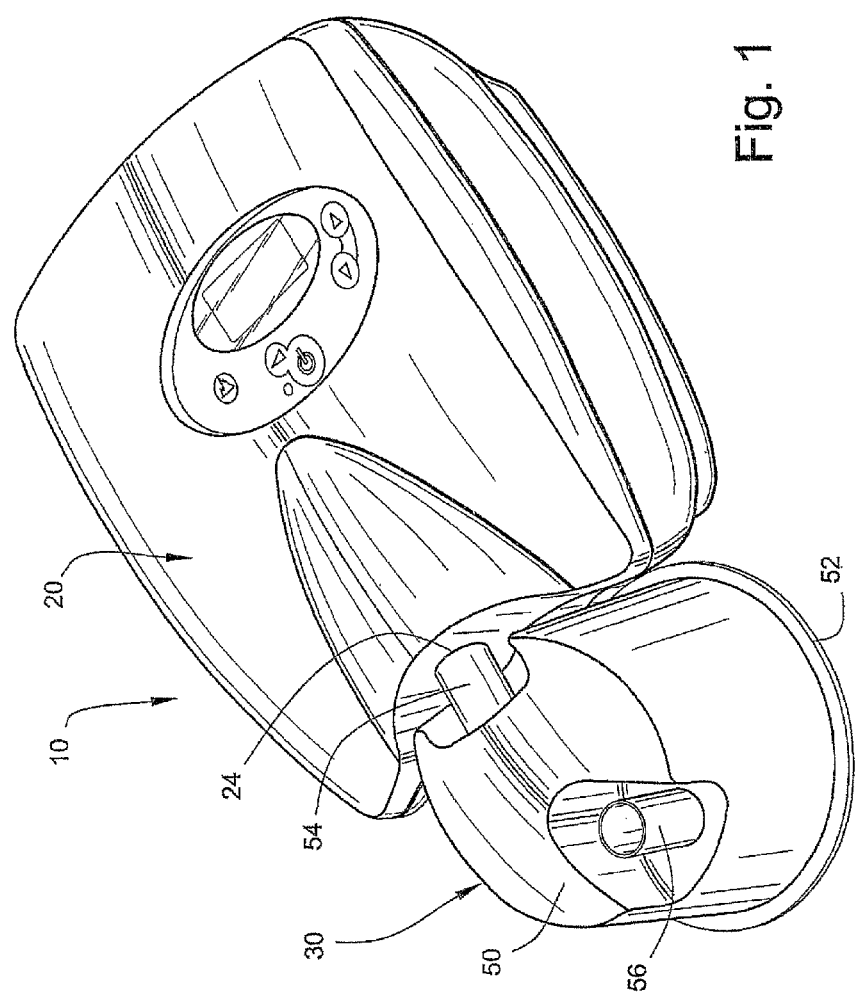
FIG. 1 is a perspective view of a CPAP device according to an embodiment of the invention.
Figure 2:
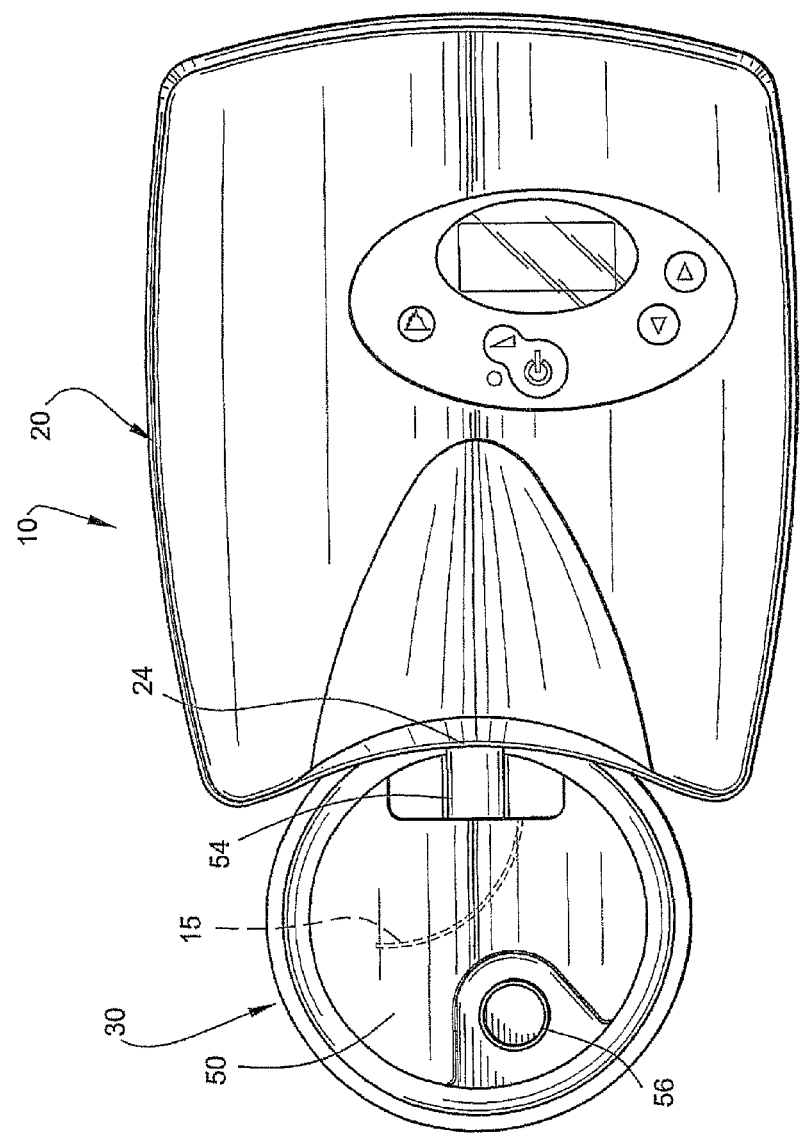
FIG. 2 is a top view of the CPAP device shown in FIG. 1.
Figure 3:
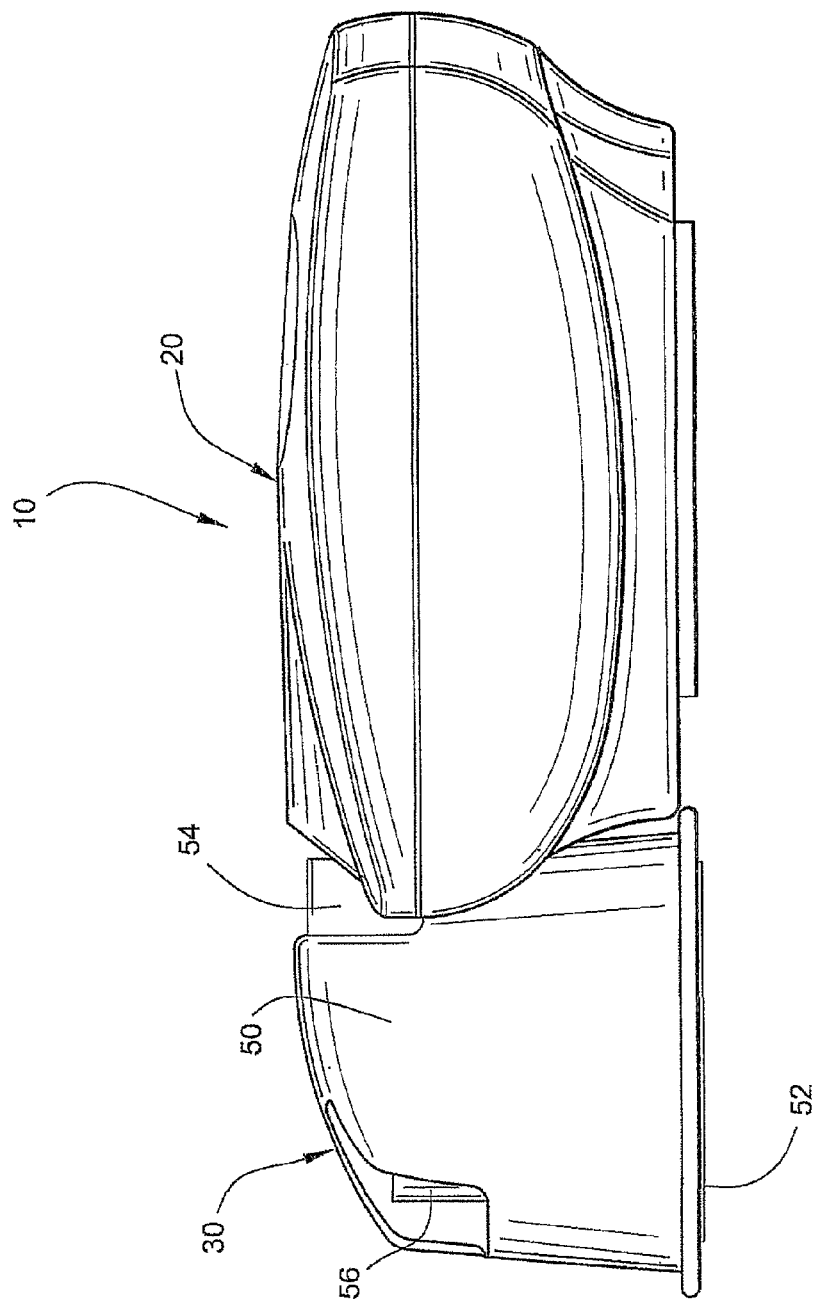
FIG. 3 is a side view of the CPAP device shown in FIG. 1.
Figure 4:
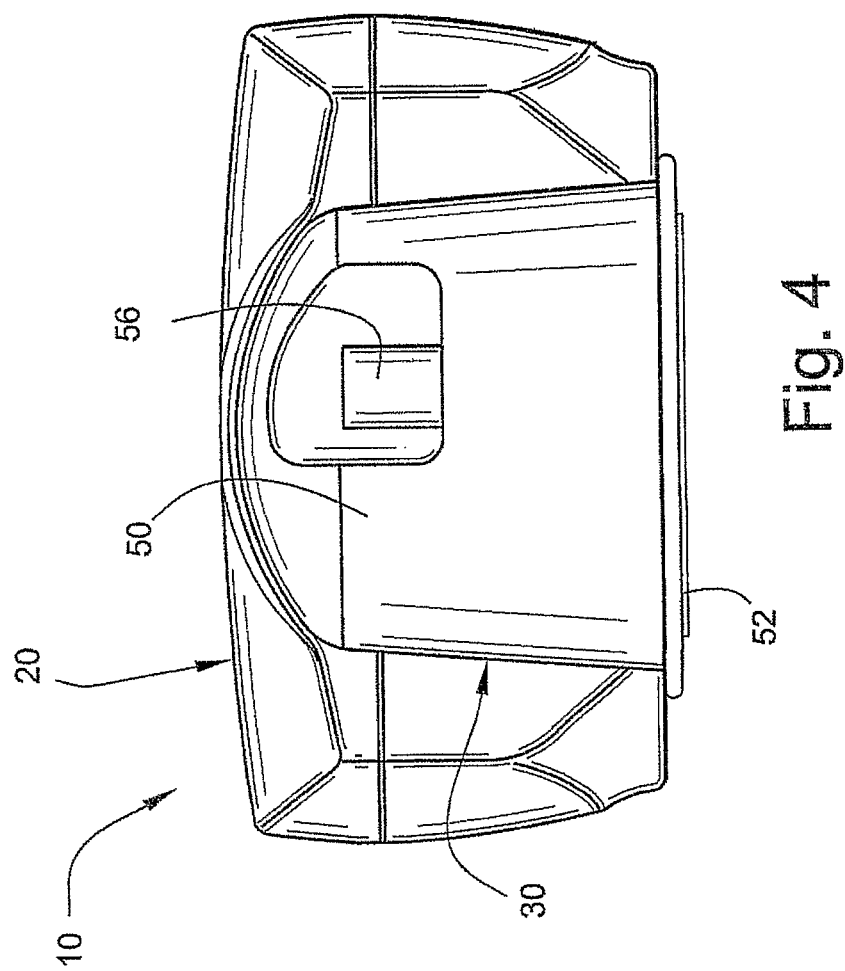
FIG. 4 is an end view of the CPAP device shown in FIG. 1.
Figure 23:
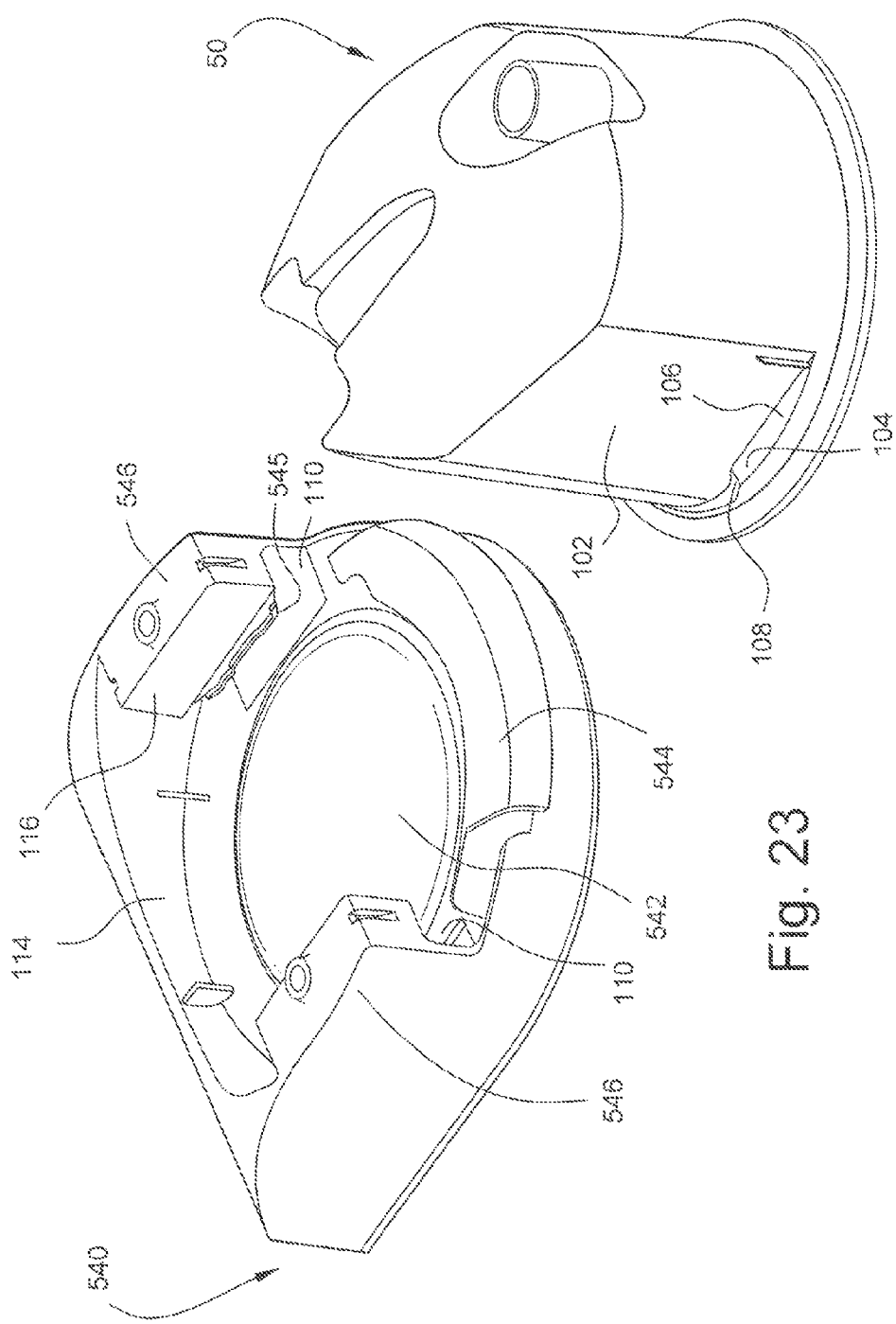
FIGS. 23-25 illustrate a cradle according to another embodiment of the present invention using a front guard and at least two pressure pads.
Figure 25:
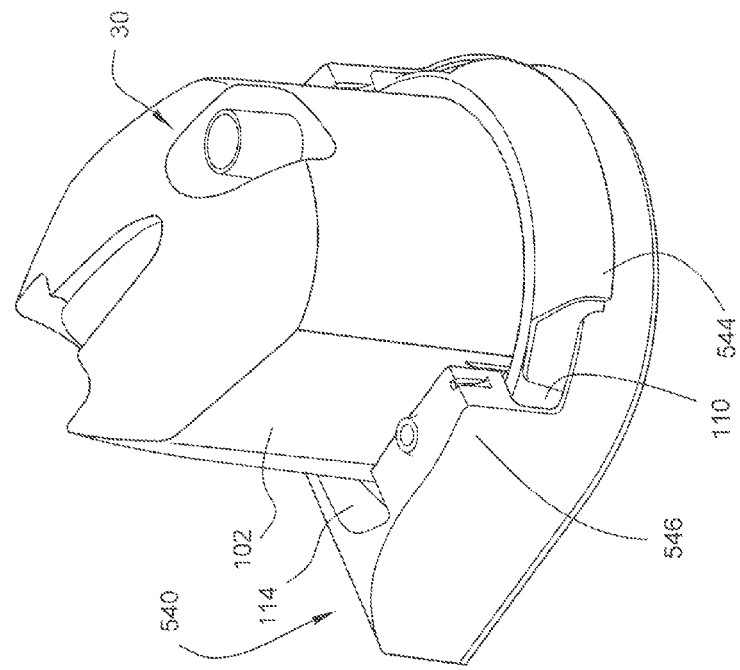
Figure 24:
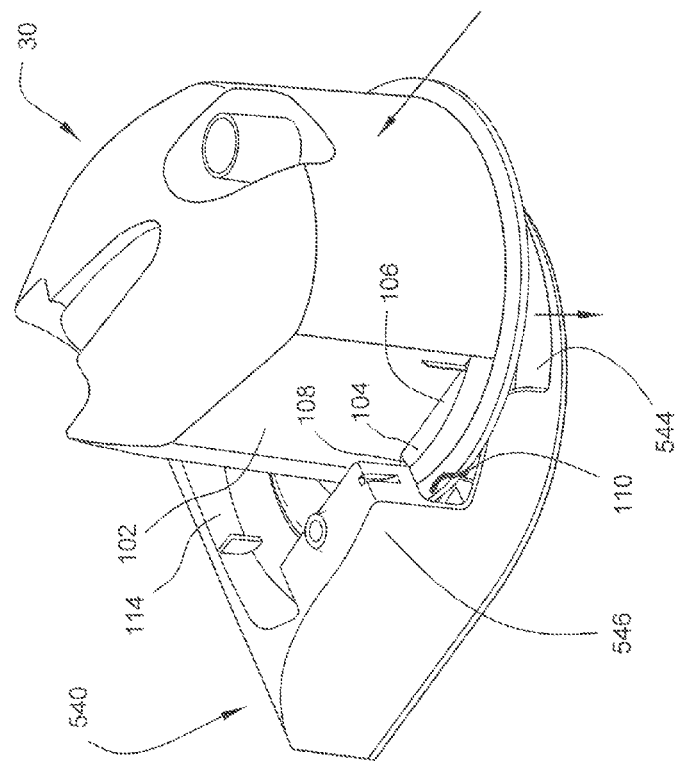

As best shown in FIG. 2, the tub 50 may include a curved baffle 15 adjacent the outlet end of the inlet 54 to smoothly change the direction of the air flow by gently guiding the air flow around the tub 50 while limiting the loss of pressure. Also, the base plate 52 may be in the form of a heat conducting base plate. Specifically, the base plate 52 may be formed of a heat conducting material, e.g., aluminum sheet. In addition, as best shown in FIG. 23, the tub 50 may include upstanding generally planar side walls 102 and a rear wall 112. The tub 50 may also include a shoulder 104 extending horizontally outwards from a lower portion of each upstanding generally planar side wall 102 of the humidifier tub. Each shoulder 104 may include a main portion 106 and a ramped portion 108. The main portion 106 may have a substantially level upper surface, while an upper surface of the ramped portion 108 may taper down toward the rear wall 112 of the humidifier tub 50.

In an embodiment, the humidifier 30 and tub 50 may be structured such as the humidifier and tub described in U.S. Patent Application No. 60/707,949, entitled "Humidifier Tub For CPAP Device", filed Aug. 15, 2005, the contents of which are incorporated in its entirety by reference herein. Also, in an embodiment, the flow generator 20 may be structured and controlled such as the flow generator described in U.S. Patent Application No. 60/707,951, entitled "Low Cost CPAP Flow Generator and Humidifier Assembly", filed Aug. 15, 2005, the contents of which are incorporated in its entirety by reference herein.

3. Seal Between Humidifier and Flow Generator

Figure 5:
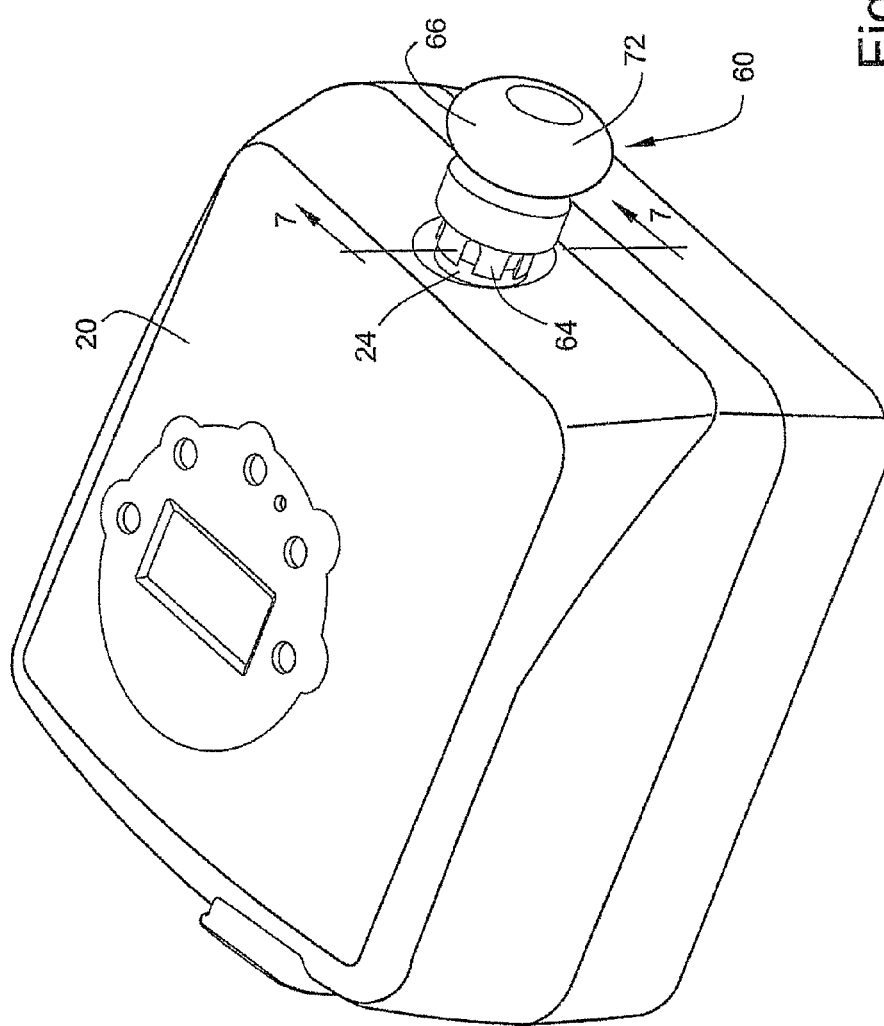
FIG. 5 illustrates a blower with a seal/connector according to an embodiment of the present invention.
Figure 6:
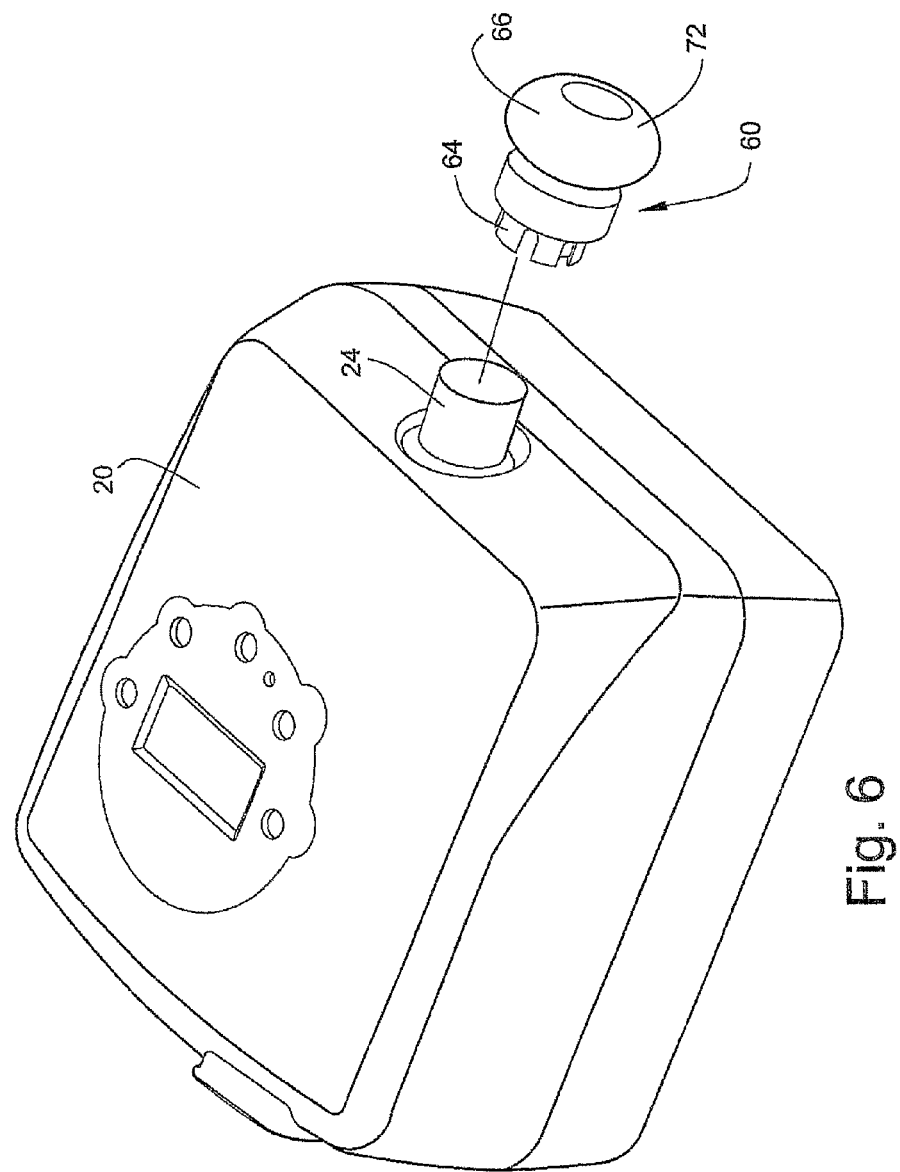
FIG. 6 illustrates the blower and seal/connector of FIG. 5 in an exploded position.
Figure 7:
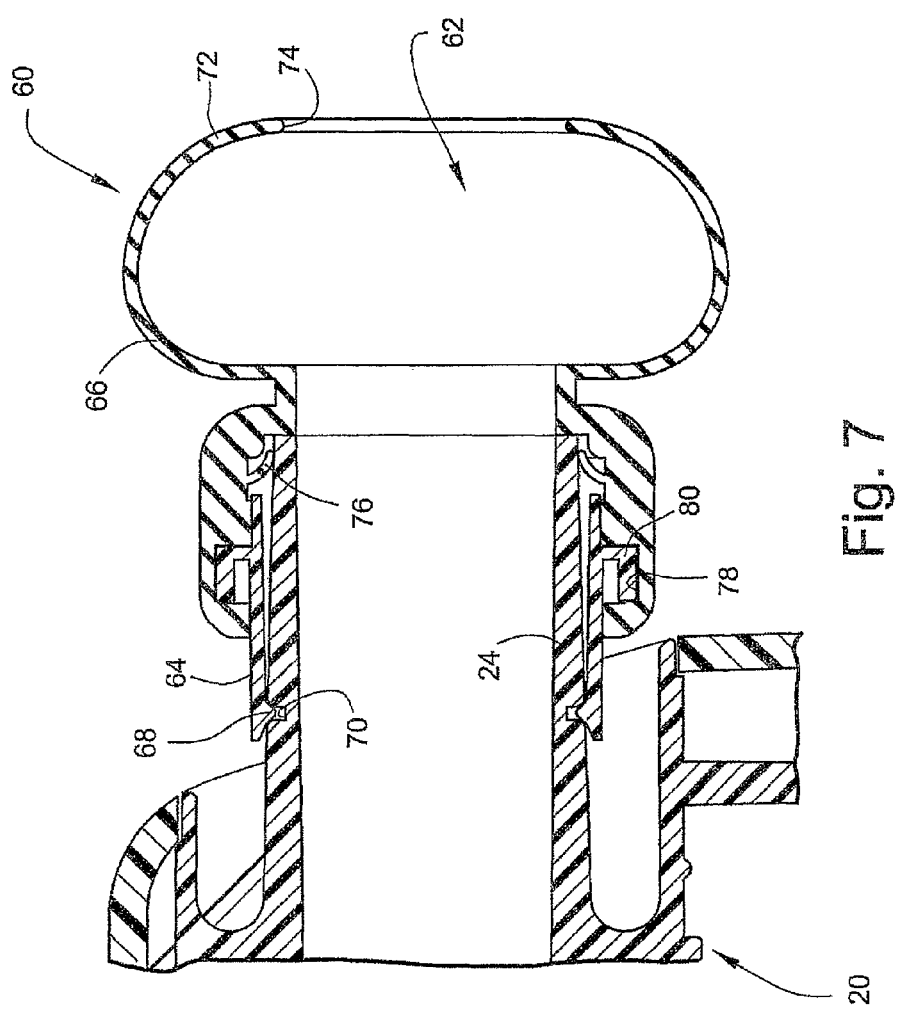
FIG. 7 is a cross section along section 7-7 of FIG. 5.
Figure 10:
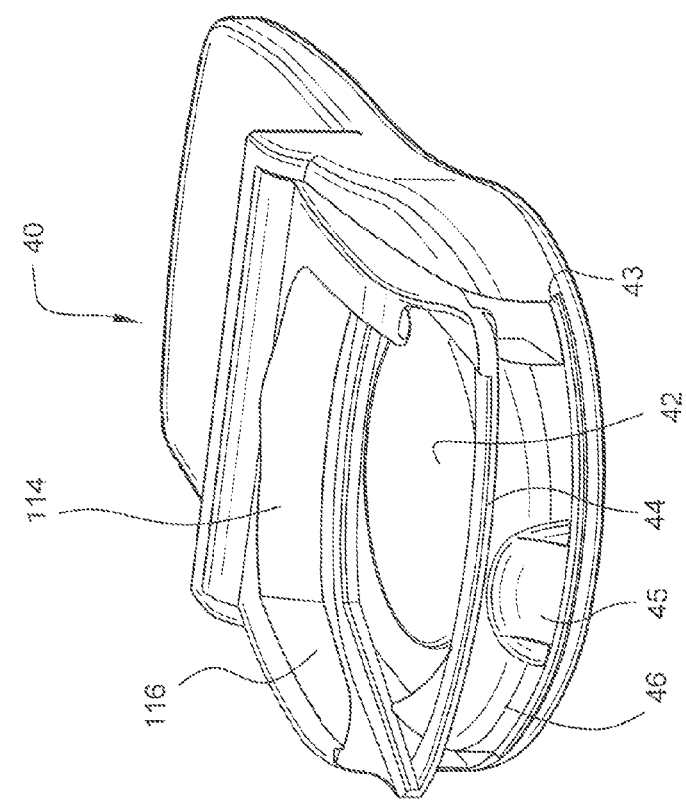

FIGS. 5-7 illustrates a connector 60 according to an embodiment of the present invention. The connector 60 interconnects the outlet 24 of the flow generator 20 and the inlet 54 of the tub 50. Moreover, the connector 60 provides a pressure-activated or 'self-energizing' face seal that provides a seal between the flow generator 20 and the tub 50. The seal accommodates misalignment and manufacturing tolerances as described below.

As illustrated, the connector 60 provides a channel 62 (FIG. 7) to deliver pressurized air from the flow generator 20 to the humidifier tub 50. In the illustrated embodiment, the connector 60 is removably attached to the flow generator 20 and is structured to sealingly engage with the inlet 54 of the tub 50.

As best shown in FIG. 7, the connector 60 includes two components that are coupled to one another. Specifically, the connector 60 includes a firm frame attaching portion 64 and a flexible sealing portion 66. The firm frame attaching portion 64 is preferably constructed of a plastic material and includes an attachment structure that enables secure attachment to the outlet 24 of the flow generator 20. For example, the attachment structure may be in the form of a snap-fit clip that includes one or more protrusions 68 adapted to engage within a corresponding groove 70 provided in the outlet 24 with a snap fit, as shown in FIG. 7. However, the attachment structure may have other suitable configurations.

The flexible sealing portion 66 comprises a bellows-type conforming face seal 72 preferably made from silicone or other similar material that does not provide problems with creep in use. The bellows-type conforming face seal 72 comprises an aperture 74 that is adapted to abut the inlet 54 of the humidifier tub 50. The flexible sealing portion 66 further includes an internal sealing element 76, e.g., wiper seal, that independently seals to the outlet 24 of the flow generator 20 to prevent air leakage through the connection between the flow generator 20 and the humidifier 30. Any means of providing a seal between the flow generator 20 and humidifier 30 is encompassed within the scope of the invention. For example, the internal sealing element 76 may be in the form of a compression sealing ridge or a wiper seal. The flexible sealing portion 66 is constructed such that it preferably does not have any split lines (from the tooling) on the outer sealing face that may interfere with obtaining a satisfactory pressure seal.

In addition, the flexible sealing portion 66 includes an interlocking structure that is structured to interlockingly engage a complementary interlocking structure provided on the firm frame attaching portion 64. In the illustrated embodiment, the sealing portion 66 includes a groove 78 that interlocks with a protrusion 80 provided on the frame attaching portion 64. This arrangement interlocks the sealing portion 66 to the frame attaching portion 64. However, the sealing portion 66 may be coupled to the frame attaching portion 64 in other suitable manners.

Alternatively, the entire connector 60 may be made of silicone or a silicone-like material with differing rigidity characteristics for the firm frame attaching portion 64 and the flexible sealing portion 66. For example, as shown in FIG. 8A, the connector 60 may have a one-piece construction and the frame attaching portion 64 may have a cylindrical structure adapted to sealingly engage the outlet 24 of the flow generator 20.

Preferably, the connector 60 has a round shape to provide minimal out-of-mold distortion. The face seal 72 of the flexible sealing portion 66 has approximately 2 mm to 3 mm interference from the nominal contact point to ensure sufficient contact when the connector 60 is pushed against the inlet 54 of the humidifier tub 50. The aperture 74 on the sealing face 72 may be larger than the inlet 54 of the tub 50 in order to accommodate the various misalignment and manufacturing tolerances of the connector 60 to outlet 24 of the flow generator 20, to ensure sufficient passage of air flow through the connector 60.

Advantageously, the face seal 72 provides for tolerance in movement in all directions while aligning the humidifier tub 50 and the flow generator 20. For example, the face seal 72 is flexible axially (forwards and backwards), laterally (upwards, downwards, and/or sideways), angularly, pivotally, and/or rotationally. Preferably, the face seal is flexible in all directions, although it may be more flexible in some but more rigid in others.

The face seal 72 may be flexible within a predetermined range. For example, the face seal 72 may be axially and/or laterally flexible within a range of about 1-5 mm, preferably about 2-3 mm. However, the face seal 72 may be axially and/or laterally flexible less than 1 mm or greater than 5 mm. Also, the face seal 72 may be angularly, pivotally, and/or rotationally flexible within a range of about 1-10°, preferably about 3-6° or about 5°. However, the face seal 72 may be angularly, pivotally, and/or rotationally flexible less than 1° or greater than 10°.

In use, the firm frame attaching portion 64 of the connector 60 is securely attached to the outlet 24 of the flow generator 20 and the bellows-type conforming face seal 72 on the flexible sealing portion 66 protrudes therefrom. The air inlet 54 of the humidifier tub 50 is positioned adjacent to or abutting the face seal 72. When pressurized air flows out through the outlet 24 of the flow generator 20, the face seal 72 fills with air and establishes a pressurized face seal with the inlet 54 of the humidifier tub 50.

FIGS. 8B and 8C illustrate an embodiment of the connector 60 forming a seal with the inlet 54 of a humidifier tub. As shown in FIG. 8B, the connector 60 is positioned adjacent the inlet 54 such that the bellows-type conforming face seal 72 is spaced from the inlet 54. As pressurized air flows out through the outlet of the flow generator (as indicated by the arrow), the face seal 72 fills with air and expands into engagement with the axial end or axially facing surface of the inlet 54 as shown in FIG. 8C. That is, the face seal 72 balloons outwardly to form a cylindrical face seal with the inlet 54.

The bellows-type conforming face seal 72 provides a flexible bellows or gusset that allows the face seal 72 to self align with the inlet 54. That is, the flexibility and freedom of movement of the face seal 72 (e.g., in all directions within a predetermined range) allows the face seal 72 to form a seal with the inlet 54 even if they are misaligned. Specifically, the face seal 72 can still form a seal with the inlet 54 even if the axis of the connector 60 is not aligned with the axis of the inlet 54. This arrangement accommodates the various misalignments that may occur between the connector 60 and the inlet 54.

Although the connector 60 has been described as being attached to the outlet 24 of the flow generator 20, in an alternative embodiment the connector 60 may be attached to the inlet 54 of the humidifier tub 50 and the flexible sealing portion 66 may abut the outlet 24 of the flow generator 20. In a further embodiment, the connector 60 may be permanently attached to either the outlet 24 of the flow generator 20 or the inlet 54 of the humidifier tub 50. However, the connector 60 is preferably a separate component that can be easily replaced or removed for cleaning or sterilization purposes.

4.0 Mechanism for Retaining Humidifier in Cradle

The CPAP device 10 may include a cradle (e.g., cradle 40 in FIGS. 9-12) structured to support the humidifier tub 50 in an operative position with respect to the flow generator 20. The cradle may include a front wall 114, side walls 116 and a heater plate that includes a heating element, e.g., a ceramic heating element. In use, the cradle receives the humidifier tub 50 so that the heating element is in thermal contact with the heat conducting base plate 52 (FIG. 3) of the humidifier tub 50. This arrangement allows water contained within the humidifier tub 50 to be heated to provide sufficient moisture to the air so that patients will be comfortable. In addition, the front wall 114 of the cradle faces the rear wall 112 of the humidifier tub 50 when the humidifier tub 50 is docked within the cradle 40. Also, the side walls 116 of the cradle 40 are configured to face the side walls 102 of the humidifier tub 50 such that the humidifier tub 50 is properly aligned with respect to the cradle 40 as the humidifier tub 50 is slid in the assembly direction (FIGS. 9-12 and 23-26).

The cradle may provide one or more of the following functional features for the humidifier tub 50: allow the humidifier tub 50 to be correctly oriented with respect to the flow generator 20; securely lock the humidifier tub 50 within the cradle such that it cannot be easily pulled out during use; ensure good thermal contact between the humidifier tub 50 and the heater plate present in the cradle; allow easy docking of the humidifier tub 50, especially for frail, elderly users; and for safety reasons, limit access to hot areas of the humidifier chamber when heat is being transferred from the heater plate to the heat conducting base plate 52 of the humidifier tub 50, once the humidifier tub 50 is docked within the cradle.

Advantageously, the cradle as described in the various embodiments herein pushes the humidifier tub downwards onto a fixed heater plate rather than forcing the heater plate upwards against the humidifier tub. The fixing of the hot plate in the cradle improves and simplifies the electrical ensures that the hot plate is sealed against water entry, which sealing is more difficult if the hot plate is movably mounted on the cradle. In this type of arrangement, a spring that forces the humidifier tub into engagement with the heater plate may be disengaged during installation of the humidifier tub within the cradle. The disengagement of the spring reduces friction forces for installation thus making installation easier and consequently minimizing friction damage to the heater plate, cradle, and humidifier tub. After installation of the humidifier tub, the spring may be reengaged to simultaneously secure the humidifier tub within the cradle and force the base plate of the humidifier tub against the heater plate to provide good thermal contact between them.

4.1 Cradle with Securing Catch

FIGS. 9-12 illustrate a cradle 40 according to an embodiment of the present invention. As illustrated, the cradle 40 has a securing catch 44 that lifts up and down to enable release or insertion of the humidifier tub 50. The securing catch 44 may be hinged. The lifting up of the securing catch 44 also disables or releases a spring that pushes the humidifier tub 50 down against the heater plate 42 (see FIGS. 9 and 10). After insertion of the humidifier tub 50 along the arms of the catch 44, closure of the catch 44 re-engages the spring to ensure a good thermal connection between the humidifier tub 50 and the heater plate (see FIGS. 11 and 12). Releasing the spring (e.g., by lifting the catch) substantially reduces the forces that have previously acted against freely inserting or removing the humidifier tub. The catch 44 also locks the humidifier tub 50 within the cradle 40 such that it cannot be pulled out during use, e.g., by pulling the air delivery tube. Specifically, a stop 46 is positioned in front of the humidifier tub 50 when the catch 44 is closed to lock the humidifier tub in place. Also, the stop 46 may provide a ridge or protrusion 43 adapted to lock the catch 44 in a closed position. In addition, a groove 45 may be provided in the stop 46 to provide a finger access that facilitates access to the catch 44. The catch 44 also prevents access to the hot heater plate 42 when the humidifier tub 50 is inserted, especially access to the front of the hot heat conducting base plate 52. The gaps between the sides of the tub and the cradle are smaller than the size of a finger (or less) to prevent accidental burning of the patient. The catch provides a "clicking" sound when the tub is properly docked thereby providing audio/tactile feedback to the patient.

4.2 Cradle with Sliding Docking Portion

FIG. 13 illustrates a cradle 240 according to another embodiment of the present invention. In this embodiment, the cradle 240 includes a docking portion 244 that is slidable between a humidifier tub locking position and a humidifier tub unlocking position (FIG. 13). The slidable mechanism may be similar to that used in loading a CD or DVD, for example, and may include a spring to facilitate movement into the humidifier tub unlocking position. In the humidifier tub unlocking position as shown in FIG. 13, the docking portion 244 is slidably extended from the cradle 240 to enable release or insertion of the humidifier tub 50. In the humidifier tub locking position, the docking portion 244 is slidably retracted into the cradle 240 to secure the humidifier tub 50 to the cradle 240. In the illustrated embodiment, the docking portion 244 includes a pin 241 that is adapted to releasably engage a ramp 243 provided on the cradle 240 to releasably lock the docking portion in the humidifier tub locking position. However, the docking portion 244 may be locked in other suitable manners. Also, a spring-loaded arm 246 may be provided to ensure a good thermal connection between the humidifier tub 50 and the heater plate of the cradle 240.

4.3 Cradle with Pivoting Docking Portion

FIGS. 14A, 14B, and 15 illustrate a cradle 640 according to another embodiment of the present invention. In this embodiment, the cradle 640 includes a docking portion 644 that is pivotable about a hinge 641 between a humidifier tub locking position (FIG. 14A) and a humidifier tub unlocking position (FIG. 14B). The cradle 640 includes a spring 648 that biases the docking portion 644 into the humidifier tub locking position. In the humidifier tub unlocking position as shown in FIG. 14B, the docking portion 644 is pivoted downwardly against bias from the spring 648 to enable release or insertion of the humidifier tub 50. In the humidifier tub locking position as shown in FIG. 14A, the docking portion 644 is pivoted upwardly by the spring 648 to secure the humidifier tub 50 to the cradle 640. FIG. 15 is an isolated view of the docking portion 644 and illustrates retaining members 645 that push down on the humidifier tub 50 (e.g., the lateral edges).

4.4 Cradle with Spring-Biased Clamping Edge

FIG. 16 illustrates a cradle 340 according to another embodiment of the present invention. In this embodiment, a lever or button (e.g., an actuator button 345) is provided on the cradle 340 that is adapted to release a spring 344 connected with a clamping edge 346, e.g., a pressure pad. In use, the humidifier tub 50 is inserted into the cradle 340 and the lever or button is actuated to release the spring-biased clamping edge 346 which clamps or frictionally secures the base of the humidifier tub 50 between the cradle 340 and the clamping edge 346. The clamping edge 346 provides downwardly directed pressure to ensure good thermal contact between the base of the humidifier tub 50 and the heater plate.

4.5 Cradle with Pivotable Front Guard and Pivotable Humidifier Retaining Portion FIGS. 17-22 illustrate a cradle 440 according to another embodiment of the present invention. In this embodiment, the cradle 440 includes two separate hinges 443, 444 that allow independent movement of a front guard 445 and a humidifier retaining portion 446, respectively. The front guard 445 is pushed or pivoted downwardly which in turn lifts the humidifier retaining portion 446 so it can pivot in an upward direction (as shown in FIGS. 17, 20, and 22). This subsequently allows easy insertion of the humidifier tub 50 into the humidifier retaining portion 446. The humidifier retaining portion 446 has planar upstanding side walls adapted to receive and engage sides of the humidifier tub 50 therein. Once the humidifier tub 50 is inserted within the humidifier retaining portion 446, the front guard 445 is released which allows both the front guard 445 and the humidifier retaining portion 446 to clasp the humidifier tub 50 and move the humidifier tub downwardly against the heater plate of the cradle 440 (see FIGS. 18, 19, and 21). Thus, the front guard 445 clamps the humidifier retaining portion 446 in a closed position. In an embodiment, a spring provides a bias to force the front guard 445 and the retaining portion 446 into a closed or humidifier retaining position.

4.6 Cradle with Front Guard and Pressure Pads

Figure 27:
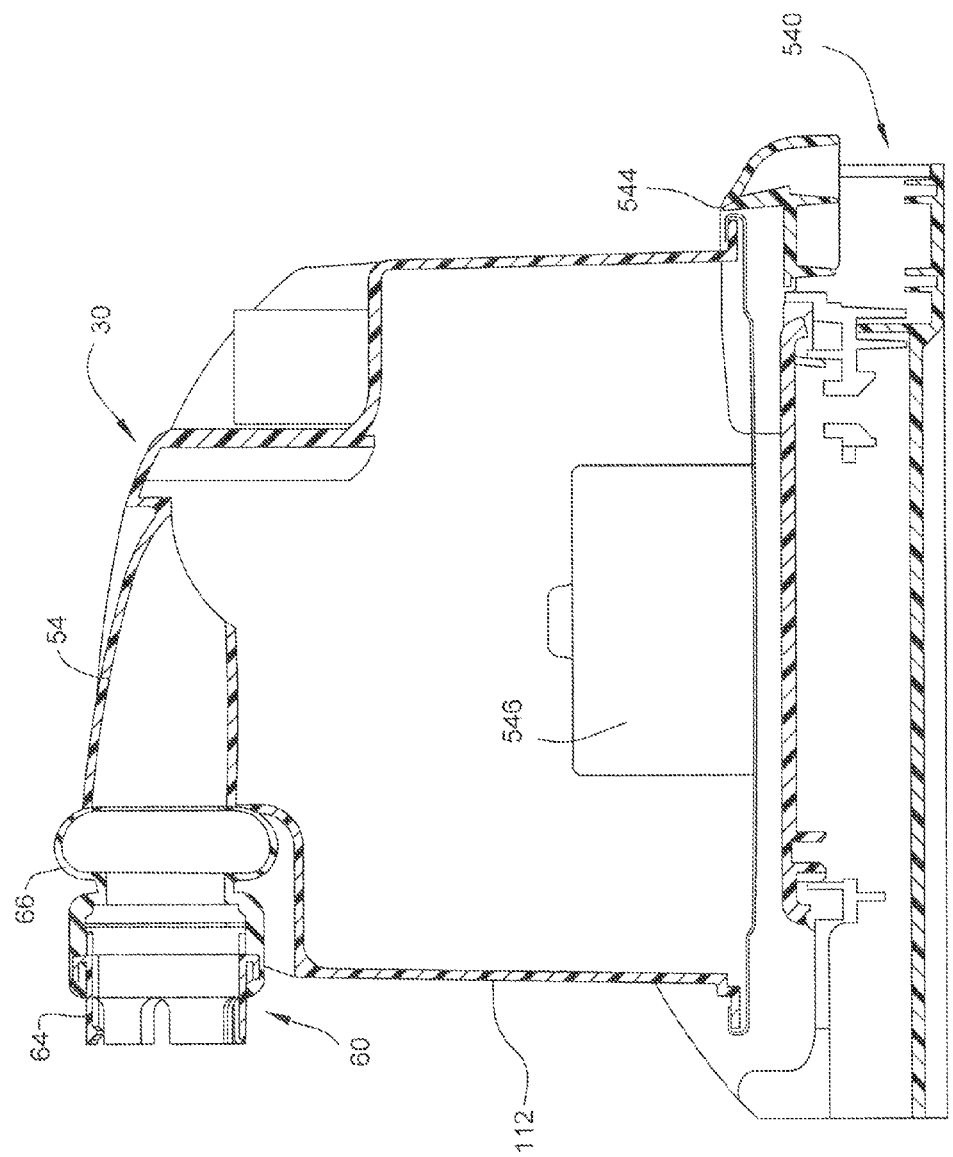
FIG. 27 is a cross-sectional view through the humidifier tub and cradle shown in FIG. 26.

FIGS. 23-27 illustrate a cradle 540 according to yet another embodiment of the present invention. In this embodiment, the cradle 540 includes a front guard or stop 344 and at least two pressure pads 546. In the illustrated embodiment, a pressure pad 546 is positioned on each side of the cradle 540 so that each pressure pad 546 is offset from a receiving side of the cradle 540 so that each side of the cradle includes a C-shaped channel adapted to slidingly receive a respective shoulder 104 of the humidifier tub 50 with the ramped portions 108 being received before the main portions 106. A spring 545 is attached to each pressure pad 546. The spring 545 is configured to force the respective pressure pad 546 in a downward direction toward the bottom of the cradle 540. The front guard or stop 544 includes a spring that forces the front guard or stop 544 upwardly to protect against access to the cradle 540 and prevent the humidifier tub 50 from falling out when installed. To install the humidifier tub 50 to the cradle 540, the front guard stop 544 is pushed downwardly, thereby allowing the humidifier tub 50 to access the cradle 540 (see FIG. 24). The shoulders 104 of the humidifier tub 50 are then inserted underneath each of the pressure pads 546 thereby causing the pressure pads 546 to be deflected upwards against biasing of the springs 545. This allows the humidifier tub 50 to slide into the cradle 540 (see FIGS. 25-27). Once the humidifier tub 50 is located within the cradle 540, the pressure pads 546 supply the force to maintain the base of the humidifier tub 50 against the heater plate 542. In addition, once the humidifier tub 50 is fully inserted in the cradle 40, the front guard or stop 544 is moved vertically relative to the humidifier tub 50, thereby preventing withdrawal of the humidifier tub 50 in a direction opposite the installation direction (i.e., withdrawal direction). In an embodiment, movement of the front guard or stop 544 is coordinated with actuation of the pressure pads 546. Preferably, the pressure pads 546 are made of smooth material that provides low friction against the humidifier tub 50 when it is inserted into the cradle 540. FIGS. 26 and 27 illustrate the humidifier tub 50 located within the cradle 540 and the inlet 54 of the humidifier tub 50 engaged with the connector 60 shown in FIGS. 5-7.

4.7 Water Damage Mitigation

In addition to the protection afforded by the tub design, the flow generator also has one or more water damage mitigating features.

System goals: The combined system (the flow generator and humidifier) should be able to prevent water entry into the flow generator from scenarios where the unit (flow generator and humidifier) is tipped up to 60° in any direction (e.g., backwards or sidewards). Even though the flow generator and/or humidifier is ideally designed to prevent water entry into the flow generator, the flow generator should be capable of handling spill-back (e.g., about 100 ml) from the humidifier. Spill-back can occur if water is accidentally introduced directly via the outlet port. The device should not be damaged, and remain safe, with 100 ml introduced, assuming the device remains in the horizontal operating position. It should be possible to drain any such water that has entered the flow generator (contained within the Outlet Muffler/sump). Furthermore, the flow generator should satisfy the IPX1 rating requirements, and the requirements of IEC60601.1, to cope with external spillage of water by user.

Figure 28:
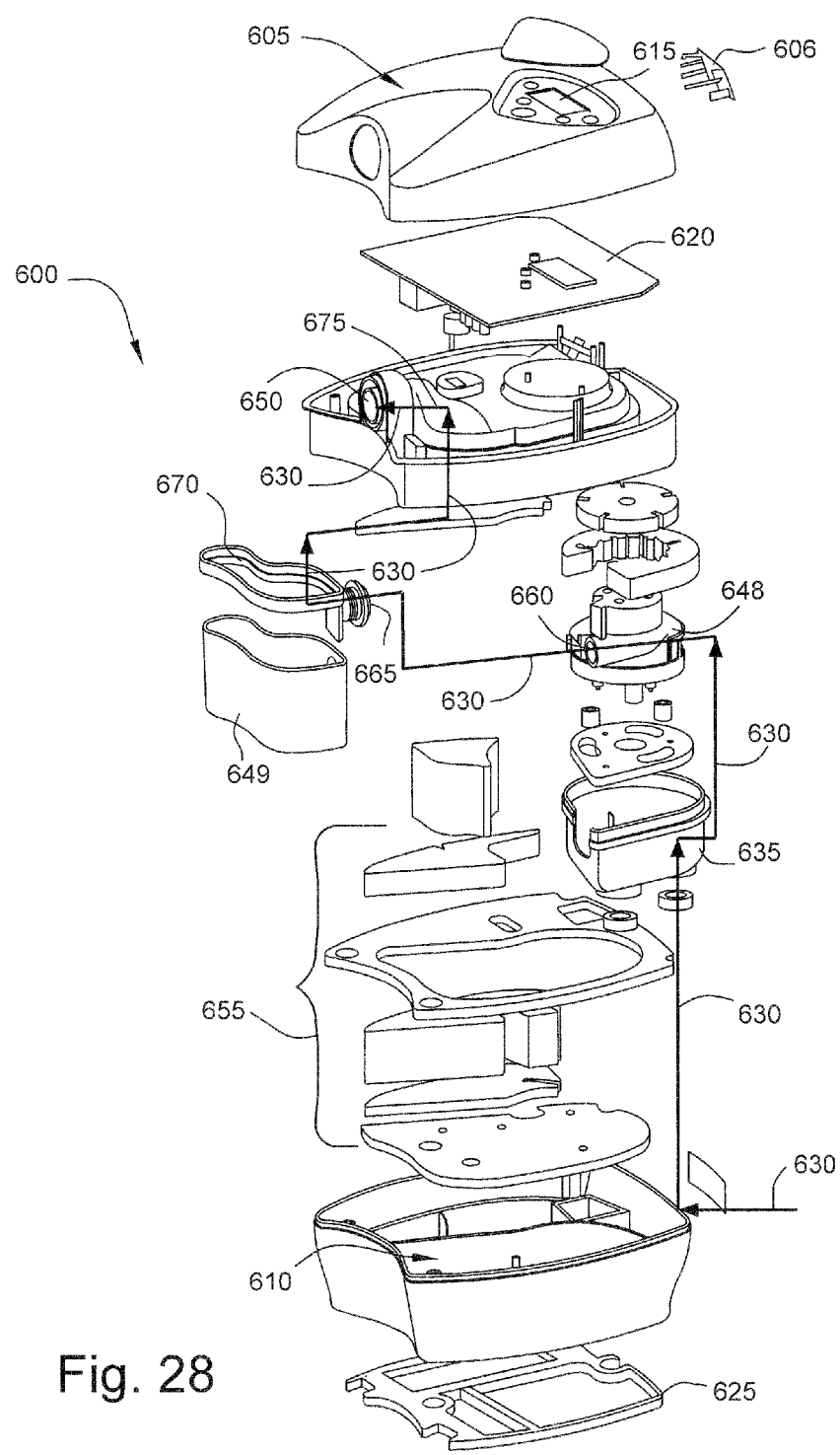
FIG. 28 is an exploded view of a flow generator according to an embodiment of the present invention.

One or more of the above goals can be achieved by implementation of the illustrative flow generator design shown in FIG. 28. FIG. 28 shows a flow generator 600 having a top case 605 and a bottom case 610. Top case 605 is provided with a keypad 615 that is operably coupled to a main PCB 620 with SMPS. Bottom case 610 is provided with base rubber feet 625. Arrows 630 schematically show the approximate path of air as it flows into, through and out of the flow generator 600. The bottom case 610 includes an inlet that directs incoming air to a motor chamber 635 that houses a motor 648. The motor 648 pressurizes the air and directs it to a sound muffler 649 that provides acoustic noise reduction. From the muffler 649, the pressurized gas exits via an outlet 650 that is in communication with an air delivery conduit. Sound insulation materials 655 may be provided, but these are preferably outside the air path.

The ability to cope with water intake at the flow generator air outlet 650 is achieved in this example by having the muffler 649 act essentially as a water sump/pump, where water cannot reach the electronics or the motor unless the device is intentionally tipped over and/or tilted backwards.

Water that has entered the flow generator 600, and is contained in the muffler 649, can be drained by tilting the flow generator forward for water to exit the air delivery port. The outlet 650 of flow generator 600 is arranged such that when the device is tipped forward it is the lowest point of the volume where water is trapped. Otherwise, the water will simply evaporate over time.

Other water mitigation features include the following features, each of which can be used alone or in combination with one or more of the other features:

Mounting the blower air inlet downwards, allowing spill back from the Humidifier to drain out of the blower inlet (into the Fan Cover) and away from the motor;

Having a very large volume (essentially the vacant space of bottom case—much larger than 100 ml) outside of and lower than the blower, so that water spill back has to completely fill this chamber before it can reach the motor;

Placing all electronics at the top of the device well away from internal water; and/or Placing the electrical interfaces (all cable connections including power) not only high on the device but above the air inlet opening where spilled water could enter the device.

For IPX1 and IEC60601.1 tests, sealing should be provided on the joints between keypad 615 and top case 605. Top case 605 shrouding 606 may also be constructed to form an "awning" over the power inlet and humidifier communications sockets. The joint between the top and bottom cases is designed to be noise tight.

The geometry of the flow generator layout is such that the sump chamber of the muffler 649 and the flow generator outlet port 650 are not axially aligned with a motor outlet 660. As shown in FIG. 28, the motor outlet 660 directs the pressurized gas to a fitting 665 that is in communication with the chamber. The fitting 665 is formed as part of, or is otherwise provided to a gasket seal 670 that follows the contour of the chamber. While the lower portion of the seal 670 contacts the chamber, the upper portion of the seal contacts a cover member or portion 675 that may be integrally formed with the blower outlet, etc.

Figure 29:
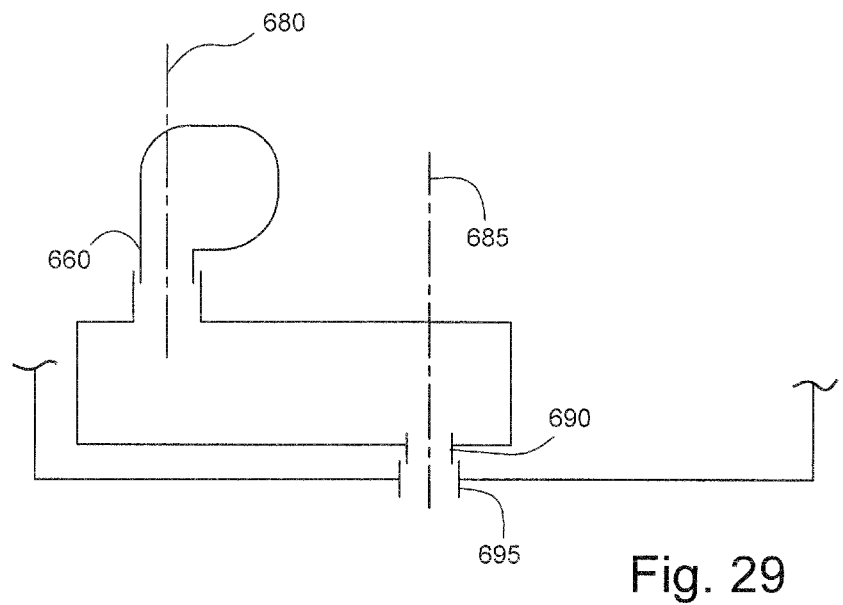
FIG. 29 is a schematic drawing illustrating the general architecture of a portion of a flow generator according to an embodiment of the present invention.

As schematically shown in FIG. 29, the axis 680 of the motor outlet 660 is offset from the axis 685 of the chamber outlet 690 and/or blower outlet 695. Thus, any water that enters the chamber from the humidifier will not be directly channeled to the motor outlet 660.

Figure 30:
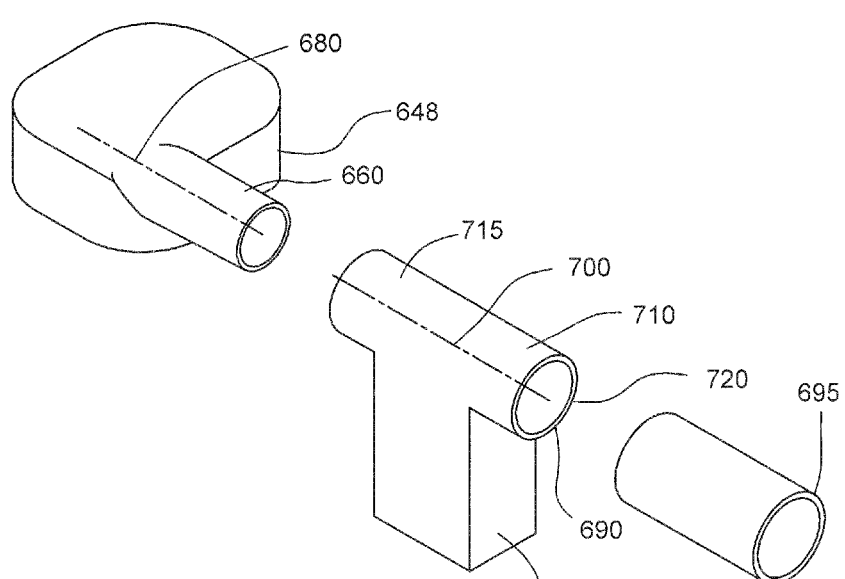
FIG. 30 is a schematic exploded view of a portion of a flow generator according to an embodiment of the present invention.

In an alternative shown in FIG. 30, the axis 680 of the motor outlet 660 can be aligned with the axis 700 of the chamber/blower outlet 690, 695, yet any water from the humidifier is not directly channeled to the motor outlet 660 because a chamber 705 is formed on a lower part of a connecting tube 710 that connects the motor outlet to the flow generator outlet. The tube has inlet and outlet portions 715, 720. The chamber 705 is provided to store a volume of water that may be accidentally introduced into the flow generator from the humidifier. This water will evaporate and/or will be reintroduced into the air path to add extra humidity, or the water can simply be emptied out by tilting or by use of a drain. The arrangement in FIG. 30 can be used in the flow generator shown in, for example, FIG. 14 of US patent application publication no. US 2005/0103339 A1, incorporated herein by reference in its entirety.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A continuous positive airway pressure (CPAP) device comprising:
   a humidifier tub including a heat conducting base plate; and
   a cradle defining a receiving area configured to laterally receive the humidifier tub and support the humidifier tub in an operative position, the cradle a comprising:
     a heater plate configured to communicate with the base plate of the humidifier tub;
     a retaining mechanism configured to retain the humidifier tub in the cradle; and
     a biasing structure arranged to provide a biasing force that forces the base plate and the heater plate together into thermal engagement,
   wherein when the cradle is in an upright operating position, the biasing structure is positioned at a periphery of the receiving area and is offset from a receiving side of the cradle so that the humidifier tub occupies a portion of the receiving area before engaging the biasing structure as the humidifier tub is laterally received by the cradle.

2. A CPAP device according to claim 1, wherein the biasing structure includes at least one spring that forces the base plate into engagement with the heater plate.

3. A CPAP device according to claim 1, wherein the retaining mechanism includes a securing catch that lifts up and down to enable release or insertion of the humidifier tub.

4. A CPAP device according to claim 1, wherein the retaining mechanism includes a front guard that enables release or insertion of the humidifier tub.

5. A CPAP device according to claim 1, further comprising a flow generator provided to the cradle and in communication with the humidifier tub.

6. A CPAP device according to claim 5, wherein the flow generator includes a motor having a motor outlet, a muffler chamber having an inlet coupled to the motor outlet and a muffler outlet in communication with a flow generator outlet.

7. A CPAP device according to claim 6, wherein an axis of the motor outlet is offset from an axis of the muffler outlet and/or the flow generator outlet.

8. A CPAP device according to claim 6, wherein the muffler chamber is structured to store a predetermined amount of water that may be inadvertently introduced into the flow generator outlet from the humidifier tub.

9. A CPAP device according to claim 8, wherein the predetermined amount of water is 100 ml.

10. A CPAP device according to claim 6, wherein said muffler chamber includes an upper part conduit portion and a lower storage portion integrally formed with the upper part conduit portion.

11. A CPAP device according to claim 5, wherein the cradle and/or humidifier tub is configured to orient the humidifier tub in a predetermined position with respect to the flow generator.

12. A CPAP device according to claim 1, further comprising a locking structure configured to secure the humidifier tub relative to the cradle.

13. A CPAP device according to claim 1, wherein the heater plate includes a ceramic heating element.

14. A CPAP device according to claim 1, wherein the biasing force is in a downward direction.

15. A CPAP device according to claim 1, wherein the biasing structure is provided at a lateral periphery of the receiving area.

16. A method for retaining a humidifier tub to a cradle, comprising:
   providing a cradle including a retaining mechanism and a biasing structure;
   moving the retaining mechanism to a first position that enables insertion of the humidifier tub;
   laterally sliding the humidifier tub into a receiving area defined by the cradle;
   bringing the humidifier tub into engagement with the biasing structure after a portion of the humidifier tub has already been laterally slid into the receiving area; and
   moving the retaining mechanism to a second position that secures the humidifier tub in an operative position,
   wherein when the cradle is in an upright operating position, the biasing structure applies a biasing force from a lateral periphery of the receiving area to force a heat conducting base plate of the humidifier tub and a heater plate of the cradle toward each other and into thermal engagement with each other.

17. A method according to claim 16, wherein the biasing structure includes at least one spring.

18. A method according to claim 16, wherein the biasing structure forces the humidifier tub downward toward the heater plate of the cradle.

19. A method according to claim 18, wherein the retaining mechanism is moved to the second position and the biasing structure is enabled after the humidifier tub is fully installed in the cradle.

20. A humidifier assembly adapted to be coupled to a flow generator, the humidifier assembly comprising:
   a cradle supporting a tub and having a heater plate, the tub having an inlet positioned on a rear wall of the tub and an outlet located on an upper side of the tub, the inlet being adapted to be in fluid communication with an output from the flow generator, the outlet of the tub being adapted to be in fluid communication with an air delivery conduit;

the tub including a heat conducting base plate provided to a bottom portion of the tub and adapted to be in thermal contact with the heater plate of the cradle when the tub is positioned within the cradle by sliding the tub from front to back relative to the cradle, the tub and the base plate defining a chamber that is adapted to receive a volume of water, wherein the chamber is configured so that a supply of pressurized air received from the flow generator through the inlet of the tub collects moisture through contact with water within the tub before continuing on to the outlet of the tub; and a connector configured to be positioned adjacent the inlet of the tub, the connector including an attaching portion and a flexible sealing portion formed in one piece, the flexible sealing portion defining a face seal of silicone, the face seal comprising an aperture configured to be adjacent to or abut a flat surface surrounding the inlet of the tub when the tub is properly docked on the cradle, wherein the flexible sealing portion has a diameter that is greater than a diameter of the attaching portion and the flat surface surrounding the inlet of the tub remains outside of the aperture of the face seal.

21. A humidifier assembly according to claim 20, wherein the face seal comprises a conforming, bellows-type seal.

22. A humidifier assembly according to claim 21, wherein the bellows-type seal includes an internal channel configured to be positioned adjacent the inlet of the tub.

23. A humidifier assembly according to claim 22, wherein the attaching portion includes a sealing element.

24. A humidifier assembly according to claim 23, wherein the flexible sealing portion is constructed such that the flexible sealing portion does not have any split lines.

25. A humidifier assembly according to claim 23, wherein the aperture on the face seal is larger than an inlet aperture of the inlet of the tub.

26. A humidifier assembly according to claim 23, wherein the face seal is conformable along an axis of the inlet of the tub.

27. A humidifier assembly according to claim 26, wherein the face seal is flexible, upwards, downwards, and/or sideways, angularly, pivotally, and/or rotationally to accommodate misalignment and/or manufacturing tolerances.

28. A humidifier assembly according to claim 26, wherein the face seal is conformable and flexible within a predetermined range.

29. A humidifier assembly according to claim 28, wherein the face seal is axially and/or laterally flexible within a range of 1-5 mm.

30. A humidifier assembly according to claim 29, wherein the face seal is configured to form a seal with the inlet of the tub even if the axis of the connector is not aligned with the axis of the inlet.

31. A humidifier assembly according to claim 30, wherein the tub includes a baffle adjacent the inlet, the baffle including a curved surface to promote circulation and water pickup.

32. A humidifier assembly according to claim 31, wherein the base plate comprises aluminum.

33. A humidifier assembly according to claim 32, wherein the attaching portion is attached to a structure configured to receive a flow of breathable gas from the flow generator.

34. A humidifier assembly according to claim 33, wherein the face seal comprises a pressure-activated seal.

35. A humidifier assembly according to claim 34, wherein the attaching portion of the connector is configured to be removably attached to the structure that receives the flow of breathable gas from the flow generator and the flexible sealing portion protrudes therefrom, the inlet of the tub being configured to be positioned adjacent to or abut the face seal such that when pressurized air flows out through the outlet of the flow generator, the face seal fills with air and establishes a pressurized face seal with the inlet of the tub.

36. A humidifier assembly according to claim 35, wherein the face seal is configured to be spaced from the inlet of the tub, in an initial position, and, as pressurized air flows into the tub, the face seal fills with air and expands into engagement with an axially facing surface of the inlet of the tub.

37. A humidifier assembly according to claim 35, wherein the face seal of the flexible sealing portion has 2 mm to 3 mm interference from a nominal contact point to ensure sufficient contact when the inlet of the tub and the connector make contact on each other.

38. A humidifier assembly according to claim 20, wherein a maximum volume of water is several hundred milliliters.

39. A humidifier assembly according to claim 20, wherein the cradle has a biasing structure configured to provide a biasing force that forces the base plate and the heater plate together into thermal engagement, and wherein the tub includes a surface extending from a side wall of the tub and the surface of the tub extending from the side wall is configured to slidingly engage an underside of the biasing structure when the tub is sliding from front to back relative to the cradle.

40. A continuous positive airway pressure (CPAP) device including:

a flow generator to generate pressurized gas in the range of 4-28 cm $H_2O$; and a humidifier assembly adapted to be coupled to the flow generator, the humidifier assembly comprising:

a cradle having a heater plate provided to a bottom surface of the cradle;

a tub configured to be slidingly received and supported by the cradle and having an inlet positioned on a rear wall of the tub and an outlet located on an upwardly facing surface of the tub, the inlet being adapted to be in fluid communication with an output from the flow generator when the humidifier assembly is coupled to the flow generator, the outlet of the tub being adapted to be in fluid communication with an air delivery conduit in use;

the tub including a heat conducting base plate provided to a bottom portion of the tub and adapted to be in thermal contact with the heater plate of the cradle when the tub is positioned within the cradle by sliding the tub from front to back relative to the cradle, the tub and the base plate defining a chamber that is adapted to receive a volume of water, wherein, the chamber is configured to receive pressurized air from the flow generator through the inlet of the tub so that the pressurized air collects moisture through contact with water within the tub before continuing on to the outlet of the tub; and a connector positioned adjacent the inlet of the tub, the connector including an attaching portion and a flexible sealing portion formed in one piece, the flexible sealing portion defining a face seal of silicone, the face seal comprising an aperture that is adjacent to or abuts a flat surface surrounding the inlet of the tub when the tub is properly docked on the cradle, wherein the flexible sealing portion has a diameter that is greater than a diameter of the attaching portion, and the flat surface surrounding the inlet of the tub remains outside of the aperture of the face seal.

41. A CPAP device according to claim 40, further comprising a structure in communication with the flow generator and the humidifier assembly, the attaching portion of the connector being connected to the structure.

42. A CPAP device according to claim 41, wherein the cradle is structured to support the tub in an operative position with respect to the flow generator.

43. A CPAP device according to claim 42, wherein the cradle is structured to push the tub downwards onto the heater plate.

44. A CPAP device according to claim 43, further comprising a spring to bias the heater plate and the base plate into good thermal contact with one another.

45. A CPAP device according to claim 44, wherein the cradle includes a securing catch that lifts up and down to enable release or insertion of the tub.

46. A CPAP device according to claim 45, wherein the securing catch includes a stop positioned in front of the tub when the securing catch is closed to retain the tub in place.

47. A CPAP device according to claim 45, wherein the securing catch is structured to prevent access to the heater plate when the tub is inserted, including access to the front of the base plate.

48. A CPAP device according to claim 45, wherein the cradle includes upstanding side walls to engage sides of the tub upon sliding insertion of the tub into the cradle when docking.

49. A CPAP device according to claim 48, wherein the side walls include generally planar surfaces.

50. A CPAP device according to claim 49, wherein gaps between the sides of the tub and the cradle are dimensioned to be smaller than the size of a finger.

51. A CPAP device according to claim 45, wherein the securing catch is structured to provide a clicking sound when the tub is properly docked thereby providing audio and/or tactile feedback.

52. A CPAP device according to claim 43, wherein the cradle further comprises a retaining structure configured to receive sides of the tub upon initial insertion of the tub into the cradle and initially direct the base plate over the heater plate and direct the base plate into contact with the heater plate upon full insertion of the tub in the cradle.

53. A CPAP device according to claim 40, wherein the cradle defines a receiving area configured to slidingly receive and support the tub, the heater plate is located at a bottom surface of the receiving area,
wherein the cradle further includes a biasing structure configured to provide a biasing force that forces the base plate and the heater plate together into thermal engagement,
wherein the tub is configured so that a side portion of the tub slides directly beneath the biasing structure when the tub is slidingly received in the receiving area, and
wherein the tub is configured so that a front portion of the tub slides across the heater plate of the cradle before the side portion engages the biasing structure when the tub is slidingly received in the receiving area.

54. A continuous positive airway pressure (CPAP) device comprising:
a humidifier tub including a heat conducting base plate; and
a cradle to support the humidifier tub in an operative position, the cradle comprising:
a heater plate configured to communicate with the base plate of the humidifier tub; and
a retaining structure with lateral portions,
wherein the retaining structure is configured to retain the humidifier tub in the cradle and is configured to lift up and down to enable release or insertion of the humidifier tub in a receiving area defined by the cradle,
wherein the lateral portions are configured to provide a downwardly directed force to ensure good thermal contact between the base plate of the humidifier tub and the heater plate, and
wherein the receiving area of the cradle is structured to laterally receive a portion of the tub before the tub engages the lateral portions.

55. A CPAP device according to claim 54, wherein the retaining structure includes at least one spring that forces the base plate into engagement with the heater plate.

56. A CPAP device according to claim 55, further including a one piece face seal configured to be adjacent an inlet of the humidifier tub, the face seal having an attaching end and a flexible, compliant sealing portion configured to contact a planar surface of the tub surrounding the inlet of the tub upon docking the tub relative to the cradle.

57. A CPAP device according to claim 56, further comprising a flow generator in communication with the humidifier tub.

58. A CPAP device according to claim 57, wherein the flow generator includes a motor having a motor outlet in communication with a flow generator outlet.

59. A CPAP device according to claim 58, wherein an axis of the motor outlet is oriented to be offset with an axis of the flow generator outlet.

60. A CPAP device according to claim 54, further comprising a spill-back sump positioned in front of an inlet of the humidifier tub, to store a predetermined amount of water that may be inadvertently introduced toward a flow generator outlet from the humidifier tub.

61. A CPAP device according to claim 60, wherein the predetermined amount of water is about 100 ml.

62. A CPAP device according to claim 54, wherein the retaining structure receives sides of the humidifier tub upon initial insertion of the humidifier tub into the cradle and initially directs the base plate over the heater plate and directs the base plate into contact with the heater plate when the humidifier tub is fully inserted in the cradle.

63. A continuous positive airway pressure (CPAP) device, comprising:
a flow generator to generate a pressurized gas flow in a range of 4-28 cm $H_2O$;
a humidifier assembly to humidify the pressurized gas flow, the humidifier assembly comprising:
a tub configured to store liquid and including an inlet configured to receive the pressurized gas flow and direct the pressurized gas flow into contact with the liquid, a heat conducting base plate provided to a bottom portion of the tub, and an outlet configured to deliver the pressurized gas flow to an air delivery conduit in use, and
a cradle configured to support the tub in an operative position to receive the pressurized gas flow, the cradle including a heater plate in contact with the base plate of the tub in the operative position, a retaining mechanism configured to retain the tub in the cradle and to bring the base plate into engagement with the heater plate, and a spring configured to bias the heater plate and the base plate toward each other and into good thermal contact with each other; and
a connector including an inlet to receive the pressurized gas flow from the flow generator, an outlet to deliver the pressurized gas flow to the inlet of the tub, and a conforming, bellows-type seal to seal the inlet of the tub when the tub is in the operative position and the pressurized gas flow is in the connector.

64. A CPAP device according to claim 63, wherein the retaining mechanism includes lateral portions positioned at laterally opposing side walls of the cradle,
wherein the lateral portions extend inwardly from the side walls toward an interior of the cradle,
wherein the tub includes projections extending laterally outward from respective side walls, and
wherein the tub projections are configured to engage the lateral portions of the retaining mechanism and force the base plate into engagement with the heater plate.

65. A continuous positive airway pressure (CPAP) device comprising:
a flow generator to generate a pressurized gas flow in a range of 4-28 cm $H_2O$;
a humidifier assembly configured to humidify the pressurized gas flow, the humidifier assembly comprising:
a tub adapted to store liquid, the tub including an inlet to receive the pressurized gas flow and direct the pressurized gas flow into contact with the liquid, and an outlet configured for communication with an air delivery tube;
a heat conducting base plate positioned on a bottom portion of the tub; and
a cradle configured to support the tub in an operative position to receive the pressurized gas flow, the cradle comprising:
a movable front guard configured to retain the tub in the cradle;
a heater plate; and
a biasing mechanism configured to bias the heater plate into engagement with the base plate; and
a connector configured to connect an outlet of the flow generator and the inlet of the tub, the connector comprising:
a plastic attaching portion configured to guide the pressurized gas flow from the flow generator; and
a flexible sealing portion associated with the plastic attaching portion, the flexible sealing portion comprising a bellows-type conforming face seal adapted to form a seal with the inlet of the tub by abutting a surface surrounding the inlet of the tub that remains outside an aperture of the flexible sealing portion.

66. A CPAP device according to claim 65, wherein the inlet of the tub and the surface that abuts the face seal are coplanar.

67. A CPAP device according to claim 65, wherein the face seal is flexible in all directions.

68. A CPAP device according to claim 67, wherein the face seal is self-aligning.

69. A CPAP device according to claim 65, wherein the flexible sealing portion is configured to interlock with the plastic attaching portion.

70. A CPAP device according to claim 65, wherein the plastic attaching portion comprises an attachment structure configured to enable secure attachment to the outlet of the flow generator.

71. A CPAP device according to claim 65, wherein the biasing mechanism is configured to bias the tub downward.

72. A CPAP device according to claim 71, wherein the cradle is configured to support at least a portion of the tub before the tub is biased downward by the biasing mechanism.

73. A CPAP device according to claim 65, wherein the tub further includes laterally extending projections extending from respective side walls of the tub,
wherein the biasing mechanism comprises lateral portions offset from a front of the cradle and positioned at opposing lateral sides of the cradle,
wherein the lateral portions are configured to engage the laterally extending projections of the tub and bias the heater plate into engagement with the base plate, and
wherein the tub is configured so that when the tub is laterally received in the cradle, the laterally extending projections of the tub slide against respective undersides of the lateral portions.

74. A CPAP device according to claim 65, further comprising a curved baffle positioned in the tub and configured to change a direction of the pressurized gas flow.

75. A continuous positive airway pressure (CPAP) device comprising:
a humidifier tub comprising:
an inlet positioned on a rear wall of the humidifier tub;
an outlet located on a substantially horizontal surface of the humidifier tub;
upstanding side walls extending between the rear wall of the humidifier tub and a front wall of the humidifier tub;
a shoulder extending horizontally outwards from a lower portion of each side wall of the humidifier tub; and
a heat conducting base plate; and
a cradle adapted to support the humidifier tub in a fully installed position, the humidifier tub being configured to be slidingly received within the cradle in an assembly direction toward a front wall of the cradle and to be slidingly withdrawn from the cradle in a withdrawal direction away from the front wall of the cradle, the front wall of the cradle being configured to face the rear wall of the humidifier tub when the humidifier tub is docked within the cradle, the cradle comprising:
side walls configured to face the side walls of the humidifier tub such that the humidifier tub is properly aligned with respect to the cradle as the humidifier tub is slid in the assembly direction;
a C-shaped channel located at each lateral side wall of the cradle and adapted to slidingly receive a respective said shoulder of the humidifier tub;
a stop configured to prevent the humidifier tub from being removed from the cradle in the withdrawal direction when the humidifier tub is fully installed within the cradle; and
a heater plate configured to communicate with the base plate of the humidifier tub,
wherein each said shoulder of the humidifier tub comprises a main portion with an upper surface that is substantially level and a ramped portion oriented towards the front wall of the cradle in the fully installed position, and
wherein the humidifier tub is configured so that during installation of the humidifier tub in the cradle, for each said shoulder, said ramped portion engages a respective said C-shaped channel before the main portion.

76. A CPAP device according to claim 75, wherein the cradle further comprises a spring biasing mechanism configured to exert a biasing force against the humidifier tub as the humidifier tub is slid in the assembly direction such that the base plate of the humidifier tub is maintained against the heater plate of the cradle.

77. A CPAP device according to claim 76, wherein each said shoulder of the humidifier tub is configured so that when each said shoulder is inserted in the respective said C-shaped channel, the spring biasing mechanism is displaced against the biasing force.

78. A CPAP device according to claim 77 further comprising a flexible connector adapted to fluidly connect the humidifier tub to a flow generator, the flexible connector being configured to sealingly engage the inlet on the rear wall of the humidifier tub.

79. A CPAP device according to claim 75, wherein the stop is configured to prevent withdrawal of the humidifier tub in the withdrawal direction when the stop and the humidifier tub are moved relative to one another in a vertical direction and the humidifier tub is in the fully installed position.

80. A CPAP device according to claim 79, wherein the side walls of the humidifier tub are generally planar.

81. A CPAP device according to claim 80, wherein the cradle is configured through spring action to force the base plate of the humidifier tub against the heater plate of the cradle.

82. A CPAP device according to claim 75, further comprising a flexible connector adapted to fluidly connect the humidifier tub to a flow generator, the flexible connector being configured to sealingly engage the inlet on the rear wall of the humidifier tub, wherein:
- the cradle further comprises a spring biasing mechanism configured to exert a biasing force against the humidifier tub as the humidifier tub is slid in the assembly direction such that the base plate of the humidifier tub is maintained against the heater plate of the cradle,
- each said shoulder of the humidifier tub is configured so that when each said shoulder is inserted in the respective said C-shaped channel, the spring biasing mechanism is displaced against the biasing force,
- the side walls of the humidifier tub are generally planar, and
- the cradle is configured through spring action to force the base plate of the humidifier tub against the heater plate of the cradle.

* * * * *